United States Patent
Mulet et al.

(10) Patent No.: US 10,335,403 B2
(45) Date of Patent: **\*Jul. 2, 2019**

(54) NIACIN FORMULATION

(71) Applicant: Zeenar Enterprises Pty Ltd., Brighton (AU)

(72) Inventors: Xavier Mulet, Elwood (AU); Gregory Yu Foo Szto, Elwood (AU); David Kannar, Elwood (AU)

(73) Assignee: ZEENAR ENTERPRISE PTY LTD (AU)

( \* ) Notice: Subject to any disclaimer, the term of this patent is extended or adjusted under 35 U.S.C. 154(b) by 0 days.

This patent is subject to a terminal disclaimer.

(21) Appl. No.: 16/132,440

(22) Filed: Sep. 16, 2018

(65) Prior Publication Data

US 2019/0015403 A1    Jan. 17, 2019

Related U.S. Application Data

(63) Continuation of application No. 14/889,878, filed as application No. PCT/AU2014/050032 on May 9, 2014, now Pat. No. 10,105,358.

(30) Foreign Application Priority Data

May 9, 2013   (AU) ................. 2013901647
Aug. 28, 2013 (AU) ................. 2013903276

(51) Int. Cl.
  *A61K 31/455*  (2006.01)
  *A61K 9/00*    (2006.01)
  (Continued)

(52) U.S. Cl.
  CPC ............ *A61K 31/455* (2013.01); *A61K 9/006* (2013.01); *A61K 9/1075* (2013.01); *A61K 9/20* (2013.01);
  (Continued)

(58) Field of Classification Search
  None
  See application file for complete search history.

(56) References Cited

U.S. PATENT DOCUMENTS 4,981,681 A    1/1991  Tosti
6,624,148 B2   9/2003  Theoharides
(Continued)

FOREIGN PATENT DOCUMENTS

AU    2013901647    5/2013
AU    2013903276    8/2013
(Continued)

OTHER PUBLICATIONS

Advancing Niacin by Inhibiting Flushing (Sep. 11, 2009).
(Continued)

*Primary Examiner* — Robert A Wax
*Assistant Examiner* — Melissa S Mercier
(74) *Attorney, Agent, or Firm* — Akerman LLP

(57) ABSTRACT

The present invention provides a composition including an amphiphilic compound capable of self-assembling into a liquid crystalline phase; and a niacin compound. In another aspect, the present invention provides a method for the treatment of a disease state comprising administering a therapeutically effective amount of a pharmaceutical composition incorporating that composition.

21 Claims, 12 Drawing Sheets

(51) Int. Cl.
A61K 9/107 (2006.01)
A61K 31/22 (2006.01)
A61K 36/00 (2006.01)
A61K 9/20 (2006.01)
A61K 31/201 (2006.01)
A61K 45/06 (2006.01)

(52) U.S. Cl.
CPC ............ *A61K 31/201* (2013.01); *A61K 31/22* (2013.01); *A61K 36/00* (2013.01); *A61K 45/06* (2013.01)

(56) References Cited

U.S. PATENT DOCUMENTS

| | | |
|---|---|---|
| 7,115,278 B2 | 10/2006 | Theoharides |
| 7,879,375 B1 | 2/2011 | Javor |
| 10,105,358 B2 | 10/2018 | Mulet |
| 2002/0150607 A1 | 10/2002 | Manning |
| 2002/0158226 A1 | 10/2002 | Lynch |
| 2005/0119340 A1 | 6/2005 | Anderson |
| 2009/0075860 A1 | 3/2009 | Yamaguchi |
| 2011/0064712 A1 | 3/2011 | Amato |
| 2011/0086074 A1 | 4/2011 | Karatgi |

FOREIGN PATENT DOCUMENTS

| | | | |
|---|---|---|---|
| CN | 101559057 | 10/2009 | |
| CN | 101836987 | 9/2010 | |
| CN | 101897708 | 12/2010 | |
| EP | 0643965 | 3/1995 | |
| GB | 1422768 | 1/1976 | |
| WO | WO 1998/047487 | 10/1998 | |
| WO | WO-9847487 A1 * | 10/1998 | ........... A61K 9/1274 |
| WO | WO 2001/078727 | 10/2001 | |
| WO | WO 2002/005779 | 1/2002 | |
| WO | WO 2002/066014 | 8/2002 | |
| WO | WO 2004/012699 | 2/2004 | |
| WO | WO 2005/013721 | 2/2005 | |
| WO | WO 2006/106390 | 10/2006 | |
| WO | WO 2012/040623 | 3/2012 | |
| WO | WO 2014/032100 | 3/2014 | |
| WO | WO 2014/179845 | 11/2014 | |

OTHER PUBLICATIONS

Ahlstrom C, et al. (2011) Feedback modeling of non-esterified fatty acids in rats after nicotinic acid infusions. J Pharmacokinet Pharmacodyn. 38(1):1-24.
An Interview with Dr. Parsons about his new book—Cholesterol Control Without Diet! The Niacin Solution (Dec. 5, 2007), available at www.buyfl.com/InterviewParsons.pdf (15 pages).
Chang C-M, et al. (1998) Low viscosity monoglyceride-based drug delivery systems transforming into a highly viscous cubic phase. Intl J Pharm. 173(1-2):51-60.
Chen CC, et al. (2010) Effects of lipophilic emulsifiers on the oral administration of lovastatin from nanostructured lipid carriers: Physicochemical characterization and pharmacokinetics. Eur J Pharm Biopharm. 74(3):474-482.
Chuong MC, et al. (2010) Formulation of Controlled-Release Capsules of Biopharmaceutical Classification System I Drugs Using Niacin as a Model. AAPS PharmSciTech. 11(4):1650-1661.
Cooper D L, et al. (2015) Effects of formulation design on niacin therapeutics: mechanism of action, metabolism, and drug delivery. Int J Pharm. 490(1-2):55-64.
Cui X, et al. (2010) Niacin Treatment of Stroke Increases Synaptic Plasticity and Axon Growth in Rats. Stroke. 41(9):2044-2049.
Drummond CJ, et al. (2000) Surfactant self-assembly objects as novel drug delivery vehicles. Curr. Opin. Colloid Interface Sci. 4(6):449-456.
Dunbar RL, et al. (2010) Seeing red: flushing out instigators of niacin-associated skin toxicity. J Clin Invest. 120(8):2651-2655.

Gong X, et al. (2011) Lamellar Crystalline Self-Assembly Behaviour and Solid Lipid Nanoparticles of a Palmityl Pro-Drug Analogue of Capecitabine—A Chemotherapy Agent. Colloids Surf B Biointerfaces. 85(2):349-359.
Guo C, et al. (2010) Lyotropic liquid crystal systems in drug delivery. Drug Discov Today. 15(23-24):1032-1040.
Hanson J, et al. (2010) Nicotinic acid- and monomethyl fumarate-induced flushing involves GPR109A expressed by keratinocytes and COX-2-dependent prostanoid formation in mice. J Clin Invest. 120(8):2910-2919.
Hassan N, et al. (2010) Chemical permeation enhancers for transbuccal drug delivery. Expert Opin Drug Deliv. 7(1):97-112.
Houston MC, et al. (2009) Nonpharmacologic Treatment of Dyslipidemia. Prog Cardiovasc Dis. 52(2): 61-94.
International Search Report dated Jul. 31, 2014 for PCT App. No. PCT/AU2014/050032 filed May 9, 2014, which was published as WO 2014/179845 on Nov. 13, 2014 (Zeenar Enterprises Pty Ltd // Xavier Mulet et al.) (5 pages).
Isaksson C, et al. (2009) Turnover modelling of non-esterified fatty acids in rats after multiple intravenous infusions of nicotinic acid. Dose Response. 7(3):247-269.
Jacob RA, et al. (1989) Biochemical Markers for Assessment of Niacin Status in Young Men: urinary and Blood Levels of Niacin Metabolites. J Nutr. 119(4):591-598.
Kamanna VS, et al. (2009) The mechanism and mitigation of niacin-induced flushing. Int J Clin Pract. 63(9):1369-1377.
Lukasova M, et al. (2011) Nicotinic acid inhibits progression of atherosclerosis in mice through its receptor GPR109A expressed by immune cells. J Clin Invest. 121(3):1163-1173.
Mulet X, et al. (2010) High throughput preparation and characterisation of amphiphillic nanostructured nanoparticulate drug delivery vehicles. Int J Pharm. 395(1-2):290-297.
Mulet X, et al. (2012) Advances in drug delivery and medical imaging using colloidal lyotropic liquid crystalline dispersions. J Colloid Interface Sci. 393:1-20.
Neuvonen P J, et al. (1991) The bioavailability of sustained release nicotinic acid formulations. Br J Clin Pharmacol. 32(4):473-476.
Patel VF, et al. (2011) Advances in oral transmucosal drug delivery. J Control Release. 153(2):106-116.
Romier-Crouzet B, et al. (2009) Inhibition of inflammatory mediators by polyphenolic plant extracts in human intestinal Caco-2 cells. Food Chem Toxicol. 47(6):1221-1230 (Abstract only).
Science Daily. Reducing niacin intake can prevent obesity, study suggests. (May 21, 2010) World J. Gasteroenterology. (2 pages).
Shinde G, et al. (2010) Formulation and Evaluation of Mucoadhesive Tablets of Niacin Using Different Bioadhesvie Polymers. Int'l. J Pharma Bio Sci. V1(2).
Sublingual and Buccal Medication Administration in Gale Encyclopedia of Nursing and Allied Health. (2005) (5 page).
Sydenstricker VP. (1958) The History of Pellagra, Its Recognition as a Disorder of Nutrition and Its Conquest. Am J Clin Nutr. 6(4):409-414.
WebMD. Niacin (Vitamin B3) Uses, Effects (Niacin Flush) (Accessed Jan. 7, 2017) (3 pages).
Written Opinion dated Jul. 31, 2014 for PCT App. No. PCT/AU2014/050032 filed May 9, 2014, which was published as WO 2014/179845 on Nov. 13, 2014 (Zeenar Enterprises Pty Ltd // Xavier Mulet et al.) (5 pages).
Yaghmur A, et al. (2009) Characterization and potential applications of nanostructured aqueous dispersions. Adv Colloid Interface Sci. 147-148:333-342.
Yvan-Charvet L, et al. (2010) Cholesterol Efflux Potential and Antiinflammatory Properties of High-Density Lipoprotein After Treatment With Niacin or Anacetrapib. Arterioscler Thromb Vasc Biol. 30(7):1430-1438.
**Preliminary Amendment filed Nov. 9, 2015 for U.S. Appl. No. 14/889,878, filed Nov. 9, 2015 (Mulet et al. // Zeenar Enterprises Pty Ltd) (7 pages).
**Non-Final Rejection dated Feb. 1, 2017 for U.S. Appl. No. 14/889,878, filed Nov. 9, 2015 (Mulet et al. // Zeenar Enterprises Pty Ltd) (18 pages).

(56) References Cited

OTHER PUBLICATIONS

\*\*Response to Non-Final Rejection filed Jun. 1, 2017 for U.S. Appl. No. 14/889,878, filed Nov. 9, 2015 (Mulet et al. // Zeenar Enterprises Pty Ltd) (17 pages).
\*\*Final Rejection filed Aug. 22, 2017 for U.S. Appl. No. 14/889,878, filed Nov. 9, 2015 (Mulet et al. // Zeenar Enterprises Pty Ltd) (17 pages).
\*\*AFCP Response filed Jan. 17, 2018 for U.S. Appl. No. 14/889,878, filed Nov. 9, 2015 (Mulet et al. // Zeenar Enterprises Pty Ltd) (19 pages).
\*\*Summary of Examiner Interview dated Feb. 15, 2018 for U.S. Appl. No. 14/889,878, filed Nov. 9, 2015 (Mulet et al. // Zeenar Enterprises Pty Ltd) (2 pages).
\*\*Notice of Allowance dated Mar. 8, 2018 for U.S. Appl. No. 14/889,878, filed Nov. 9, 2015 (Mulet et al. // Zeenar Enterprises Pty Ltd) (9 pages).
\*\*Rule 1.132 Amendment filed Mar. 20, 2018 for U.S. Appl. No. 14/889,878, filed Nov. 9, 2015 (Mulet et al. // Zeenar Enterprises Pty Ltd) (3 pages).
\*\*Notice of Non-Compliant Information Disclosure Statement mailed Apr. 5, 2018 for U.S. Appl. No. 14/889,878, filed Nov. 9, 2015 (Mulet et al. // Zeenar Enterprises Pty Ltd) (1 page).
\*\*Rule 1.132 Amendment filed Apr. 16, 2018 for U.S. Appl. No. 14/889,878, filed Nov. 9, 2015 (Mulet et al. // Zeenar Enterprises Pty Ltd) (4 pages).
\*\*Notice of Non-Compliant Information Disclosure Statement mailed Apr. 19, 2018 for U.S. Appl. No. 14/889,878, filed Nov. 9, 2015 (Mulet et al. // Zeenar Enterprises Pty Ltd) (1 page).
\*\*Notice of Allowance dated Jun. 15, 2018 for U.S. Appl. No. 14/889,878, filed Nov. 9, 2015 (Mulet et al. // Zeenar Enterprises Pty Ltd) (6 pages).

\* cited by examiner

NIACIN FORMULATION

This application is a continuation of U.S. application Ser. No. 14/889,878 filed Nov. 9, 2015, which is a national phase application of International Application No. PCT/AU2014/050032 filed May 9, 2014, which claims priority to AU Patent Application No. 2013901647 filed May 9, 2013 and to AU Patent Application No. 2013903276 filed Aug. 28, 2013, each of which is incorporated in its entirety by reference herein.

FIELD OF THE INVENTION

The invention generally relates to formulations of niacin, methods for their preparation and methods for their use in treatment. In particular, the present invention has an application directed towards a niacin formulation for buccal administration with a therapeutically effective release profile, suitable for the treatment of conditions requiring supplementary niacin such as dyslipidaemia and related cardiovascular conditions. The present invention is also directed to a new pharmaceutical composition to assist clinicians treating patients with these conditions.

BACKGROUND OF THE INVENTION

Niacin (also known as nicotinic acid or vitamin B3) is an essential dietary constituent. Niacin deficiency leads to pellagra, which is characterised by loss of appetite, lethargy, weakness, diarrhoea, dermatitis and mental changes.

There is evidence that niacin can treat dyslipidaemia as it reduces total cholesterol, low density lipoproteins (LDL, bad' cholesterol), and triglycerides, and increases high density lipoproteins (HDL, 'good' cholesterol). For example, when added to drugs for lowering cholesterol (statins), 2 g/day of slow-release niacin taken orally was more effective than ezetimibe (Zetia) in reducing carotid intima-media thickness, a marker of atherosclerosis. Additionally, clinical trials found positive effects of niacin alone or in combination on all cardiovascular events and on atherosclerosis evolution.

Niacin is however associated with a high incidence of side effects including skin flushing, redness and burning. At therapeutic daily doses of 1.5-3 g/day, niacin often causes a painful skin flushing condition. Since the introduction of statins for lowering cholesterol, orally administered niacin has been avoided by clinicians as the side effects result in poor patient compliance. Moreover, as dyslipidaemia is an asymptomatic condition, patients are particularly less tolerant of medications causing side effects, such as niacin. Side effects with niacin administration have been a substantial limitation to its widespread use, and improvement in side effect control is required.

Immediate-release niacin is known in vitamin preparations. Extended-release niacin (Niaspan ER) has more recently become commercially available in the USA but has been associated with further problems of liver toxicity. Accordingly, there is a need for improved niacin formulations and methods of treatment which reduce the adverse side effects associated with its administration. EP 0643965 discusses administration of an oral dosage before periods of unconsciousness (eg sleep) but this has not proven to be commercially successful.

The prior art also discloses niacin compositions for oral administration and topical formulations containing niacin for transdermal delivery, see GB 1422768 and WO 2001/078727. Neither of these have been commercially successful.

Another problem facing clinicians is that the different statins now most commonly used to control cholesterol levels in patients have recently been found to be associated with serious side effects, including increased risk of diabetes and memory loss, that are not apparent to the patient. Clinicians are faced with an ever increasing, demand for cholesterol control but increased concern over the safety of the standard family of drugs used to treat it.

The features of buccal administration of some drugs is known, with the distinctive property that absorption and delivery is very quick. Some cardiac medications are administered buccally so that immediate effects are achieved. Rapid absorption of niacin via this buccal route is undesirable as it may cause skin toxicity, so a means of slowing its absorption is desirable to reduce the adverse side-effects. The other characteristic of buccal administration is that drugs administered buccally generally avoid first-pass liver metabolism, which may be significant for dosing where the drug is liver-metabolised. Accordingly, buccal administration enables a reduction in the overall dose that is required to achieve a similar effect compared to oral administration.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

The present invention provides a composition including an amphiphilic compound capable of self-assembling into a liquid crystalline phase; and a niacin compound. Upon contact with a hydrophilic solvent the amphiphilic compound forms a self-assembled structure that includes the niacin compound.

In one aspect, the present invention provides a composition suitable for buccal administration including an amphiphilic compound capable of self-assembling, into a liquid crystalline phase and a niacin. Preferably, the self-assembled structure is a cubic phase or hexagonal phase as discussed below.

In another aspect, the present invention provides a composition including an amphiphilic compound capable of self-assembling into a liquid crystalline phase and a niacin, wherein upon contact with a hydrophilic solvent the amphiphilic compound forms a self-assembled structure that includes the niacin compound. It is preferred for the composition to be suitable for buccal administration. Buccal administration includes sublingual, sublabial, delivery through the buccal vestibule and any other mucosal delivery in the mouth.

Various embodiments of the composition of the invention are set out below. The composition of the invention may include an amphiphilic compound, niacin compound and a supplement. It is preferred for the supplement to be an anti-flushing supplement. The supplement may be an anti-inflammatory agent and is preferred to be a sugar cane derived extract comprising polyphenols and/or flavonoids. The niacin compound can be niacin or a produg of niacin.

The composition of the invention may include an amphiphilic compound, niacin compound and an enhancer. The enhancer enhances the buccal delivery of the niacin compound. The composition of the invention may include an amphiphilic compound, niacin compound and polyethylene glycol (PEG). The niacin compound can be niacin or a produg of niacin.

The composition of the invention may include an amphiphilic compound, niacin compound, an enhancer and a supplement. Preferably, the enhancer is PEG. Preferably, the supplement is a sugar cane derived extract comprising polyphenols and/or flavonoids. The niacin compound can be niacin or a produg of niacin.

The composition of the invention may include an amphiphilic compound, niacin compound and a stabiliser. The stabiliser stabilises the self-assembled structures. The stabiliser is preferably a polymer stabiliser. The composition of the invention may include an amphiphilic compound, niacin compound and a poloxamer copolymer. The stabiliser is preferably, a polyethylene glycol (PEG)-propylene oxide (PPO)-polyethylene glycol (PEG) non-ionic block copolymer with an average molecular weight of 14,600. Alternatively, the stabiliser can be an antioxidant such as a tocopherol and/or vitamin C. The niacin compound can be niacin or a produg of niacin.

The composition of the invention may include an amphiphilic compound, niacin compound, a stabiliser and an enhancer. Preferably, the enhancer is PEG Preferably the stabiliser is a poloxamer copolymer. Alternatively, the stabiliser is a poloxamer copolymer. The niacin compound can be niacin, or a produg of niacin.

The composition of the invention may include an amphiphilic compound, niacin compound, a stabiliser and a supplement. Preferably the stabiliser is a poloxamer copolymer. Preferably, the supplement is a sugar cane derived extract comprising polyphenols and/or flavonoids. The niacin compound can be niacin or a produg of niacin.

The composition of the invention may include an amphiphilic compound, niacin compound, a stabiliser, an enhancer and a supplement. Preferably the stabiliser is a poloxamer copolymer. Preferably, the enhancer is PEG. Preferably, the supplement is a sugar cane derived extract comprising, polyphenols and/or flavonoids. The niacin compound can be niacin or a produg of niacin.

The composition of the invention may include an amphiphilic compound, niacin compound and a statin. Preferably, the statin is 1-10% w/w compared to the amphiphilic compound. The composition of the invention may include an amphiphilic compound, niacin compound, a statin and a stabiliser. Preferably the stabiliser is a poloxamer copolymer. The composition of the invention may include an amphiphilic compound, niacin compound, a statin and an enhancer. Preferably, the enhancer is PEG. The composition of the invention may include an amphiphilic compound, niacin compound, a statin and a supplement. Preferably, the supplement is a sugar cane derived extract comprising polyphenols and/or flavonoids. The composition of the invention may include an amphiphilic compound, niacin compound, a statin, a supplement and an enhancer. The composition of the invention may include an amphiphilic compound, niacin compound, a statin, a stabiliser and an enhancer. The composition of the invention may include an amphiphilic compound, niacin compound, a statin, a supplement and a stabiliser. The niacin compound can be niacin or a produg of niacin.

Alternatively, the composition of the invention may include a glycerol monooleate and niacin. The glycerol monooleate can be the commercial product Myverol™. The composition of the invention may include a glycerol monooleate, niacin and a supplement or glycerol monooleate (G 10), niacin and an anti-flushing supplement, preferably a sugar cane derived extract comprising polyphenols and/or flavonoids. The composition of the invention may include a glycerol monooleate, niacin and an enhancer. Preferably, the enhancer is PEG. The composition of the invention may include a glycerol monooleate, niacin and a stabiliser. Preferably the stabiliser is a poloxamer copolymer. The composition of the invention may include a glycerol monooleate, niacin, an enhancer and a supplement. The composition of the invention may include a glycerol monooleate, niacin, an enhancer and a stabiliser. The composition of the invention may include a glycerol monooleate, niacin, an enhancer, a supplement and a stabiliser.

In all embodiments of the composition of the invention, the amphiphilic compound or glycerol monooleate is capable of self-assembling in to a liquid crystalline phase upon contact with a hydrophilic solvent. The self-assembled structure formed includes the niacin compound and may include any stabiliser. It is preferred for any enhancer and/or supplement not to be included in the self-assembled structure. Preferably, the self-assembled structure is a cubic phase or a hexagonal phase.

In another aspect, the present invention provides a self-assembled structure including the composition of the invention, for example as described above, and a hydrophilic solvent.

It is preferred, for all embodiments of the composition of the invention, that the composition is pharmaceutically acceptable. All embodiments of the composition of the invention may further comprise a pharmaceutically acceptable carrier, excipient, diluent, additive, vehicle or mixtures thereof.

It is preferred, for all embodiments of the composition of the invention, that the composition is suitable for buccal administration.

The amphiphilic compound forms a self-assembled liquid crystalline phase when placed in contact with a hydrophilic solvent. The amphiphilic compound is capable of forming a self-assembled structure that includes the niacin compound. Advantageously, the self-assembled structure delays and/or prolongs release of the niacin compound, thereby improving the release kinetics of the niacin compound, which enables the rate of diffusion to be controlled. Preferably, the release rate is prolonged for up to 12 hours, more preferably 6 to 8 hours. One preferred release profile is to delay niacin release for about 30 minutes to permit absorption of other bioactives or supplements before the absorption of niacin and then permit release of niacin over the following 8 to 12 hours. One method of delaying the release of niacin is to use a niacin compound that is a prodrug of niacin, which takes time to release the niacin itself. Delay of release of niacin can also be achieved by additional ingredients such as the use of a delayed release coating to prepare coated niacin particles with delayed release properties.

Without being bound by any theory or mode of action, it is believed that prolonging release of the niacin has the advantage of minimising the blood concentration of niacin and that this is advantageous as the side effects of niacin are proportional to the maximum blood concentration. The efficacy of niacin is more closely related to the total dose than the maximum blood concentration. Thus, prolonging the release and absorption of the niacin will minimise side effects with minimal effect on the efficacy of the treatment.

It is preferred for the composition to adhere to the buccal mucosa. Alternatively or in addition, the self-assembled structures formed upon contact with a hydrophilic solvent are preferred to adhere to the buccal mucosa.

In some embodiments of the present invention, the composition physically disintegrates into particles upon contact with a hydrophilic solvent (such as saliva). Disintegration may take 2 to 10 or preferably 5 minutes. The particles include the self-assembled structures. The particles adhere to the buccal mucosa and are covered with a film, for example a micro film, of ingredients from the composition. The film assists absorption by holding the particles against the buccal mucosa and protecting the particles from disruption, for example, when the cheek rubs the gums. Disintegrating compositions of this type may be in the form of a tablet. Without being bound by theory or mode of action, it is believed that his method of mucosal adhesion assists in the desired delayed and/or prolonged release of the niacin. The niacin compound can be released from the self-assembled structure and then absorbed through the buccal mucosa. Alternatively, entire self-assembled structure(s) can absorb through the buccal mucosa and the niacin compound can be released following absorption of the self-assembled structure into the blood stream. Interstitial spaces in the buccal mucosa can be expanded with an enhancer to assist absorption. Enhancers are described further below.

Thus, in one aspect the invention provides a muccoadhesive tablet including the composition of the invention as discussed above, wherein upon administration the amphiphilic compound forms a self-assembled structure that includes the niacin compound, the tablet disintegrates into particles including the self-assembled structures; and the particles adhere to the buccal muccosa. Preferably, the particles adhered to the buccal mucosa are covered with a film of ingredients from the tablet. Preferably the self-assembled structure formed upon disintegration of the muccoadhesive tablet prolongs the release of the niacin. The muccoadhesive tablet may include an enhancer for enhancing the buccal delivery of the niacin. The muccoadhesive tablet may also contain a supplement, a stabiliser and/or a statin.

In one embodiment, a supplement is added to the composition of the invention, for example, to reduce side-effects. The supplement may be referred to as an anti-flushing supplement, where the supplement is added to reduce flushing. Flushing is a common side effect of the administration of niacin. The supplement can be administered with, before or after the niacin compound. Where the supplement is administered with the niacin compound, the supplement may be in a different composition to the niacin compound or in the same composition. Where the supplement is administered with the niacin compound it is preferred that the supplement is immediately released and release of the niacin compound is delayed by 10, 15, 20 or 30 minutes. This will allow some but preferably most of the supplement to be absorbed before a significant amount of the niacin compound is absorbed. Thus, the self-assembled structure will prolong the release of the niacin compound and in some embodiments release of the niacin compound will also be delayed. In other words, release of the niacin may be delayed for 10, 15, 20 or 30 minutes and once release commences the release is prolonged. Examples of supplements are described below.

The composition of the invention may include both a supplement and an enhancer.

Thus, in one embodiment of the present invention, the self-assembled structure formed upon contact of the composition of the invention with a hydrophilic solvent prolongs release of the niacin compound. In another embodiment of the present invention, release of the niacin compound is delayed following administration and the self-assembled structure prolongs release of the niacin compound.

The amphiphilic compound is a compound that possesses both a hydrophilic portion and a hydrophobic portion capable of forming a self-assembled structure. The amphiphilic compound can also be a mixture of amphiphiles. Amphiphiles capable of self-assembly behaviour have been described in various publications, such as, for example, Drummond and Fong (Drummond 2000), Laughlin (Laughlin 1996, 2000), and Small (Small 1986). Examples of amphiphiles that are capable of self-assembly include, but are not limited to: surfactants, lipids, and block copolymers. More specifically, the amphiphilic compound may be selected from: fatty acids, fatty alcohols, acylglycerols, glycolipids, sphingolipids, phospholipids, cholesterol and mixtures thereof. However, models to accurately predict the behaviour of such amphiphiles in a variety of media do not exist, especially when combined with a pharmaceutical active component to form a composition.

In one embodiment, the amphiphilic compound is selected from a fatty acid comprising a 6 to 24 carbon chain, preferably a 12 to 24 carbon chain, more preferably a 16 to 20 carbon chain, most preferably an 18 carbon chain. The amphiphilic compound can also be a mixture of fatty acids. In a preferred embodiment, the amphiphilic compound is selected from one or more mono- and/or di-glycerides of fatty acids comprising a 6 to 24 carbon chain, preferably a 12 to 24 carbon chain, more preferably a 16 to 20 carbon chain, most preferably an 18 carbon chain. The carbon chain may optionally have one or more double bonds such that it is unsaturated. One preferred class of amphiphilic compounds is glycerol monooleates (GMOs). In a particularly preferred embodiment the amphiphilic compound is Myverol™ 18-99k (trade mark owned by Kerry Group Services Limited) Myverol™ is generally considered a GMO despite including some non-GMO amphiphiles. Myverol™ 18-99k is produced from the reaction of glycerol with canola (low erucic acid rapeseed) oil and contains a mixture of monoacylglycerols, diacylglycerols and glycerol. The compositional analysis of Myverol™ 18-99k is detailed in Clogston (Clogston 2000) wherein Myverol™ 18-99k was found to contain 82% monoacylglycerols (consisting of 86.6% monoolein (1-Oleoyl-rac-glycerol), 7.0% monostearin (1-Stearoyl-rac-glycerol), 3.5% monopalmitin (1-monohexadecanoyl-rac-glycerol), 0.9% monoarachidin (1-Arachidonoyl-glycerol) and 2.0% unidentified monoacylglycerols), 13.4% diacylglycerols (consisting of 7.4% 1,2 diacylglycerol and 6.0% 1,3-diacylglycerol) and 4.3% glycerol.

Thus, in one embodiment the amphiphilic compound is a mixture of amphiphiles. Preferably, the amphiphilic compound contains a mixture of monoacylglycerols, diacylglycerols and glycerol. In particular, the mixture of amphiphiles is produced by reacting glycerol with canola oil. One suitable available amphiphilic compound contains 82% monoacylglycerols, 13.4% diacylglycerols and 4.3% glycerol. More particularly, the amphiphilic compound can contain:

82% monoacylglycerols consisting of 86.6% monoolein, 7.0% monostearin, 3.5% monopalmitin, 0.9% monoarachidin and 2.0% unidentified monoacylglycerols;

13.4% diacylglycerols consisting of 7.4% 1,2-diacylglycerol and 6.0% diacylglycerol, and 4.3% glycerol.

In a further embodiment, the amphiphilic compound includes (i) a mixture of a mono- and/or di-glyceride of one or more fatty acids and (ii) one or more free fatty acids.

Thus, the amphiphilic compound may include Myverol™ 18-99k and a fatty acid, such as oleic acid. In a further embodiment, the amphiphilic compound includes a self-assembling structure of monoacylglycerol and oil. In another embodiment, the amphiphilic compound includes a self-assembling structure of a fatty acid and its soap counterpart. In a further embodiment tocopherol acetate is added to the amphiphilic compound as a second gelant or stabiliser to assist formation of the self-assembled structures (see WO 2014/040623, the contents of which are incorporated by reference).

The niacin compound is niacin itself or a compound other than niacin which the body metabolises into niacin. The niacin compound includes, but is not limited to, niacin, its salts, metabolic derivatives, prodrugs, complexes and combinations thereof. Examples of compounds other than niacin itself include: nicotinyl alcohol tartrate, d-glucitol hexanicotinate, aluminium nicotinate, niceritrol and d,1-alpha-tocopheryl nicotinate. In one embodiment, the niacin compound is niacin.

In one preferred embodiment, the invention provides a composition including monoacylglycerols, diacylglycerols and niacin. The composition may further include oleic acid. Preferably the niacin is dry. The wt % of dry niacin in the composition is 50-90 wt %) of the composition. Alternatively, the amount of dry niacin in the composition can be determined in relation to the amount of amphiphilic compound. For example, the weight ratio of niacin to amphiphilic compound can be from 1:1 to 1:7, preferably 1:3 to 1:5 and more preferably, 1:3.5 to 1:4.5 or 1:4.

Alternatively, the niacin may be dissolved in a hydrophilic solvent, for example, an aqueous solvent, such as water, and/or another hydrophilic solvent, such as ethanol, to form a prehydrated self-assembled structure. A mixture of water and ethanol is the preferred hydrophilic solvent. The wt % of 100 mg/mL niacin solution in the composition is 30-70 wt %. One option is for the composition to include a niacin compound, an amphiphilic compound and a hydrophilic solvent. The composition may additionally include another active, supplement, enhancer, stabiliser or excipient as described elsewhere in the specification. The weight ratio of hydrophilic solvent in the prehydrated composition to the weight of the prehydrated composition is 1:4 to 1:1. One option is a weight ratio of 1:2. When seeking to improve the consistency of prolonged release a ratio of 1:4 is preferred. Alternatively, the weight ratio of hydrophilic solvent in the prehydrated composition to the weight of the niacin compound and amphiphilic compound is 1:4 to 1:1. One option is a weight ratio of 1:2. When seeking to improve the consistency of prolonged release a ratio of 1:4 is preferred.

The prehydrated composition described above is preferred to be suitable for buccal administration. The prehydrated composition may be administered in the form of a spray.

The present invention also provides a self-assembled structure including the composition as described above and a hydrophilic solvent. Preferably, the hydrophilic solvent is selected from the group consisting of water, water/ethanol mixture, physiological saline, buffered aqueous solution, simulated body fluids, physiological fluids or mixtures thereof. In one embodiment, the self-assembled structure is polyethylene glycol (PEG)-free.

The self-assembled structure may be selected from the group consisting of micellar (normal and reversed), lamellar, hexagonal (normal and reversed), cubic (normal discrete, reversed discrete, reversed bicontinuous—including primitive, gyroid and diamond—and reversed discontinuous), and other Intermediate phases' such as the ribbon, mesh, or non-cubic 'sponge' bicontinuous phases. In a preferred embodiment, the self-assembled structure is selected from cubic phase, hexagonal phase and mixtures thereof, preferably reversed bicontinuous cubic phase, preferably the diamond phase.

Without being bound by theory or mode of action, it is believed that the more complex the self-assembled structure, the slower the release of the niacin compound. Thus, the hexagonal and cubic, particularly diamond cubic, self-assembled structure are believed to result in the slowest release.

The self-assembled structure may be bulk phase or preferably colloidal particles, typically derived from such a bulk phase. Colloidal particles may be selected from the following group: cubosomes, hexosomes, sponge particles and mixtures thereof, preferably cubosomes.

In one embodiment, the niacin compound may be incorporated or dissolved within the self-assembled structure. Preferably, the niacin compound is non-covalently incorporated. In another embodiment, the niacin compound may form part of the self-assembled structure. In this embodiment, the niacin compound is preferably in the form of a prodrug, where for example, a compound is bound to the niacin compound, typically covalently, to form a niacin derived amphiphilic compound capable of self-assembly. In this embodiment, the niacin is not added to the amphiphilic compound in the composition but is part of the amphiphilic compound that self-assembles. Where the niacin is part of the amphiphilic compound that self-assembles, the niacin needs to be cleaved, for example by an enzyme or hydrolysis, either before or after absorption to form niacin.

The self-assembled structure may further include a polymer stabiliser. Myverol™ is an example of a preferred amphiphilic compound that is an inherently unstable lipid and benefits from stabilisation. Suitable stabilisers are those that will stabilise dispersions. Pluronic® polymers (trade mark owned by BASF), which are noneonic triblock copolymers commercially available from BASF (ie poloxamer copolymer) may be used for this purpose, eg Pluronic® F127, which is a polyethylene glycol (PEG)-propylene oxide (PPO)-polyethylene glycol (PEG) non-ionic block copolymer with an average molecular weight of 12,600 and approximately 100 PEG units and 65 PPO units. Another option is Pluronic® F108, which is a polyethylene glycol (PEG)-propylene oxide (PPO)-polyethylene glycol (PEG) non-ionic block copolymer with an average molecular weight of 14,600 and approximately 132 PEG units and 50 PPO units. Pluronic® F108 is the preferred Pluronic® polymer. Alternatively, a Myrj® polymer (trade mark owned by Uniqema Americas LLC), which is a polyoxyethylene stearate polymer, may be used as a polymer stabiliser. For example, Myrj® 59 (Polyoxyethylene (100) Stearate). Other non-limiting examples of stabilisers that could be used are proteins such as caseins, in particular β-casein; synthetic layered silicates such as Laponite™ (trade mark owned by BYK. Additives); modified cellulose; ethoxylated phytosterol, Polysorbate 80 (Polyoxyethylene (20) sorbitan monooleate) and silica particles. Antioxidants such as tocopherols, vitamin C and/or other natural antioxidants can alternatively be added to stabilise the self-assembled structures. One option is to use the vitamin E precursor tocopherol acetate and or the vitamin C precursor ascorbyl palmitate as stabilisers (see WO 2012/040623).

In another aspect, the present invention provides a pharmaceutical composition including a self-assembled structure as described above, optionally including a pharmaceutically acceptable carrier, excipient, diluent, additive, vehicle or mixtures thereof.

The pharmaceutical compositions according to the present invention may further include adjuvants that include, but are not limited to: preservatives, wetting agents, antimicrobial agents and mixtures thereof. Other adjuvants include but are not limited to: cryoprotectants, spray drying adjuvants, buffers, isotonically adjusting agents, pH adjusting materials and mixtures thereof.

The pharmaceutical compositions according to the present invention may include an additive, such as an enhancer and/or a supplement. Enhancers increase membrane permeability and/or increase the solubility of the niacin compound Enhancers include but are not limited to: alcohols, particularly ethanol, and surfactants, particularly PEG. However, the pharmaceutical composition of the invention may also be PEG-free. In an alternate embodiment, the self-assembled structure includes PEG as an enhancer. Without being bound by theory or mode of action, it is believed that PEG (and other enhancers) assist the buccal membrane to open, which is believed to assist absorption of particles of self-assembled structures. When PEG is included as an enhancer, it is preferred that PEG is 10 to 15% w/w of the composition. 12-13% why is particularly preferred. Other enhancers include chelators, surfactants, fatty acids, Azone™ (trade mark owned by Echo Therapeutics, Inc.), chitosan and its derivatives. More specifically, EDTA, menthol, Polysorbate 80, Phosphatidylcholine, sodium glycocholate, sodium taurocholate, benzalkonium chloride, Azone™, sodium taurodeoxycholate, cetylpyridinium chloride, sodium glycodeoxycholate, sodium lauryl sulphate, sodium salicylate, chitosan, methylpyrrolidinone chitosan, lauric acid, cyclodextrin, Laureth-9 and lysalbinic acid (See Hassan, N et al, Chemical permeation enhancers for transbuccal drug delivery. *Expert Opinion* 2010, 7(1), 97-112).

As discussed above, a supplement is an ingredient added to the pharmaceutical composition or administered separately to the pharmaceutical composition to either improve its overall effect and/or reduce side effects of the active niacin compound. A supplement can be a side effect minimising agent such as an anti-flushing agent, for example an anti-inflammatory agent. Examples of supplements are chocolate, polyphenols including flavonoids, anti-histamines, tocopherols such as vitamin E and its related compounds, non-steroidal anti-inflammatory drugs, serotonin inhibitors and cyclooxygenase (COX-1&2) inhibitors. In a preferred embodiment, the supplement is an anti-inflammatory agent, more preferably a sugar cane derived extract comprising polyphenols and/or flavonoids. In a preferred embodiment, the sugar cane derived extract coats the niacin compound or the sugar cane derived coats a particle containing the niacin compound. In one embodiment, the supplements are included in the dosage form with the niacin self-assembled structure. Where the supplements are included in the dosage form with the niacin self-assembled structure, the supplements do not need to be part of the self-assembled structure itself, that is, they do not need to be within the self-assembled structure with the niacin. What is required is that they are administered at about the same time for absorption with the niacin compound to exert their effects against the side-effects of niacin, such as flushing. It can be advantageous to administer the anti-flushing compounds up to 20 minutes prior to absorption of the niacin compound. This can be achieved by administering the supplements in a separate format or via co-administration using a coating or laminated carbohydrate film technologies whereby the outer layers containing these compounds are removed prior to absorption of the niacin compound, such that anti-flushing compounds are absorbed about 20 minutes before the niacin compound.

The pharmaceutical composition may further include a secondary active compound, preferably a statin. Statins are proven to lower cholesterol. The range of statin dose is from 5 to 80 mg daily. For example, the statins are generally administered in the following dosage ranges: atorvastatin 10 to 80 mg/day, fluvastatin 20 to 80 mg/day, lovastatin 10 to 80 mg/day, pravastatin 10 to 80 mg/clay, rosuvastatin 5 to 40 mg/day, and simvastatin 5 to 40 mg/day. The bioavailability of statins via oral ingestion is low, ranging from 5 to 20%. Since buccal administration enhances bioavailability by 2 to 5 times, the buccal dosage of statins added to the niacin compound may be reduced significantly, thereby reducing the side effects of statins. When used in combination with niacin and when administered by the buccal route, statins may be used in lower doses (10-30% of the effective oral dose 0.5 to 30 mg/day) thus minimising their undesirable side-effects noted above. Suitable statins include, but are not limited to: atorvastatin, fluvastatin, lovastatin, mevastatin, pitavastatin, pravastatin, rosuvastatin, simvastatin and mixtures thereof. Statins used in the invention may be hydrophobic (ie lipophilic) but are preferably hydrophilic. Hydrophilic statins, including fluvastatin, pravastatin and rosuvastatin are less toxic than lipophilic statins, including atorvastatin, lovastatin and simvastatin. In a preferred embodiment, the pharmaceutical composition may further include any one or more of fluvastatin, pravastatin and rosuvastatin.

The pharmaceutical composition according to the current invention may be dehydrated, freeze-dried, spray freeze dried or spray-dried powder.

The pharmaceutical composition may be in the form of a spray, carbohydrate film, functional food, lozenge, tablet (including a soft melt tablet), capsule (including, a gelatine capsule), and a dose form including a troche or paste. Preferably, the pharmaceutical composition is in a buccal dosage form, preferably a paste or gelatin capsule Most preferably, the pharmaceutical composition is in a gelatin capsule buccal dosage form. An alternate, preferred form for the composition is a mucoadhesive tablet, in particular, a mucoadhesive tablet that disintegrates into mucoadhesive particles as discussed above. Liquid and semi-solid pharmaceuticals can be safely delivered by containment within a gelatine capsule. These can be formulated so they rest comfortably, for example, against the gum of a patient for buccal administration. Alternatively, pullulan and hypromellose are non-animal derived alternatives to gelatin.

The amount of niacin compound that may be included in a single dosage form of the pharmaceutical composition will vary (depending upon the host treated and the particular mode of administration. Dosage unit forms will generally contain between about 100 mg to about 1,000 mg of niacin compound, preferably between about 100 mg and about 500 mg of niacin compound. Preferably, each dosage unit form includes at least, or equal to, an amount of niacin compound equivalent to about 250 mg to about 500 mg of niacin.

In a particularly preferred embodiment, the composition includes niacin, Myverol™ and suitable excipients. For example, the composition can include:
  35-50% w/w niacin
  5-15% w/w Myverol™
  and suitable excipients.
In particular, the cc composition can include:
  35-50% w/w niacin 5-15% w/w Myverol™
2-10% w/w Aerosil™ (trade mark owned by Evonik Degussa GmbH)
15-25% w/w microcrystalline cellulose
2-20% w/w Pharmaburst™ (trade mark owned by SPI Pharma Inc)
5-15% w/w croscarmellose sodium
0.5-5% w/w magnesium stearate
0-15% w/w povidone More particularly, the composition can include:
42.5% why niacin
10.6% w/w Myverol™
5.9% w/w Aerosil™
20% w/w microcrystalline cellulose
10% w/w Pharmaburst™
10% w/w croscarmellose sodium
1% w/w magnesium stearate The composition of the invention may also include stabilisers, for example:
0.5-2% w/w Pluronic™ 108 or tocopherol acetate The composition of the invention may also include an enhancer, for example:
1-10% PEG Enhancer may be added with or without stabiliser.

The composition of the invention may also include a second active such as a statin, for example:
1-10% statin A second active may be added with or without stabiliser and/or enhancer. The compositions above may also contain a supplement such as a sugar cane derived extract comprising polyphenols and/or flavonoids.

Without being bound by theory or mode of action, it is believed that the Pharmaburst disintegrant speeds disintegration of the tablet compared to the use of microcrystalline cellulose alone and the use of microcrystalline cellulose slows the disintegration of the tablet compared to the use of Pharmaburst alone. There may be dosage forms in which slower disintegration is preferred. The disintegration of the tablet may be fast while release of the niacin compound from the self-assembled structure remains slow.

In another aspect, the present invention provides a method for the treatment of a disease state comprising administering a therapeutically effective amount of a pharmaceutical composition according to the invention. Preferably, administration is to a subject identified as in need thereof. In one embodiment, the disease state is dyslipidaemia, preferably hyperlipidaemia. In another embodiment, the disease state is cardiovascular disease and/or atherosclerosis. The invention also provides a method of preventing these disease states developing by administering the pharmaceutical composition of the invention.

In another aspect, the present invention provides a use of a pharmaceutical composition according to the invention in the manufacture of a medicament for the treatment of a disease state comprising administering a therapeutically effective amount of the pharmaceutical composition. Preferably, administration is to a subject identified as in need thereof. In one embodiment, the disease state is dyslipidaemia, preferably hyperlipidaemia. In another embodiment, the disease state is cardiovascular disease and/or atherosclerosis. The invention also provides the use of the medicament to prevent these disease states developing. The invention similarly provides for a pharmaceutical composition to be used for treating or preventing these conditions in which the active ingredient is a composition of the invention or a self-assembled structure as described above.

The invention also provides for the use of a therapeutically effective amount of the composition of the invention, a self-assembled structure, a pharmaceutical composition or a muccoadhesive tablet as described in any one of the embodiments in this specification for use in treating or preventing a disease state. Preferably, administration is to a subject identified as in need thereof. In one embodiment, the disease state is dyslipidaemia, preferably hyperlipidaemia. The disease state may also be cardiovascular disease and/or atherosclerosis. The invention also provides for use of a therapeutically effective amount of the composition of the invention, a self-assembled structure, a pharmaceutical composition or a muccoadhesive tablet as described in any one of the embodiments in this specification to prevent these disease states developing. In one embodiment, administration is to a subject identified as in need of administration to prevent these disease states developing.

The invention also provides for the use of an amphiphilic compound capable of self-assembling into a liquid crystalline phase and a niacin compound in the preparation of a medicament for the treatment of a diseased state. Further, a therapeutically effective amount of the composition of the invention, a self-assembled structure, a pharmaceutical composition or a muccoadhesive tablet as described in any one of the embodiments in this specification may be used in the preparation of a medicament for use in treating or preventing a disease state as described above.

In a particularly preferred embodiment, as explained further below, the method comprises buccal administration of a therapeutically effective amount of the pharmaceutical composition. One suitable form of buccal administration is sublingual administration (under the tongue). Another suitable form of buccal administration is administration to the buccal vestibule, that is, the area inside the mouth between the lining of the cheek and the teeth/gums. A further form of buccal administration is sublabial administration, where the composition is administered under the lip. When administered in this way, the niacin diffuses into the blood through the mucosa in the mouth.

Advantageously, buccal administration avoids first pass metabolism. The combination of incorporating or complexing a niacin compound in a self-assembled structure and buccal administration has been found to reduce side effects by reducing the initial loading dose of niacin required to provide a therapeutic effect. The buccal dosage forms require less than the typical amount of the active compound generally used in other formulations to achieve the therapeutic effect. The buccal dosage form is placed in contact with the buccal membrane to thereby cause the niacin compound to be released and absorbed optimally through the mucous membranes in a buccal cavity. The combination of a self-assembled structure and buccal administration enables the rate of diffusion of the niacin compound to be controlled thereby also reducing adverse side effects. This results in improved plasma profiles and an improved pharmacokinetic profile for the niacin compound.

In another aspect, the present invention provides a method of preparing a self-assembled structure according to the invention. In one embodiment, the amphiphilic compound, niacin compound and hydrophilic solvent are mixed to form a pre-hydrated self-assembled structure. In this embodiment, the niacin compound is first dissolved in the hydrophilic solvent and then mixed with the amphiphilic compound. When the amphiphilic compound contacts the hydrophilic niacin solution, the amphiphilic compound forms a self-assembled structure including the dissolved niacin compound. The mixing may be conducted at any temperature the hydrophilic solvent is a liquid, preferably room temperature. The self-assembled structure releases the niacin compound upon contact with an appropriate solvent, such as phosphate buffered saline (PBS). Without being bound by any theory or mechanism of action, it is believed that this release of the niacin compound from the prehydrated self-assembled structure results from the niacin compound diffusing out of the self-assembled matrix. There may also be some degradation of the self-assembled matrix in viva.

In another embodiment, the present invention provides a method of preparing a self-assembled structure including the steps of mixing an amphiphilic compound, a niacin compound; and then dispersing the mixture in a hydrophilic solvent to produce a self-assembled structure. The self-assembled structure is formed in situ. For instance, for an in vivo application, the composition of the current invention may be formulated dry and then administered to form a self-assembled structure upon mixing with a hydrophilic solvent administered simultaneously or with physiological fluid in vivo. In this embodiment, the mixing is conducted at physiological temperature. In this embodiment, the amphiphilic compound and niacin compound are combined prior to mixing with the hydrophilic solvent. The amphiphilic compound and niacin compound formulation are in the form of a paste or wax Without being bound by any theory or mechanism of action, it is believed that the self-assembly of the material occurs upon contact with a solvent such as PBS or water and permits the influx of aqueous solution into the structure. Preferably this occurs at room temperature or physiological temperature. The aqueous solution is able to dissolve the niacin compound entrapped in the matrix and release it through diffusion. There may be some physical degradation of the self-assembled matrix in vivo.

The mixing may be achieved using any means known in the art, for instance, a mechanical stirrer, a magnetic stirrer, a tilting tray, or vortexing.

Preferably, the hydrophilic solvent is water, physiological saline, simulated body fluids or aqueous buffer. Examples of appropriate buffers include but are not limited to physiologically acceptable buffers, such as, for example, phosphate, phosphate buffered saline (PBS), tris(hydroxymethyl)aminomethane (Tris), 4-(2-hydroxyethyl)-1-piperazineethanesulfonic acid (HEPES), Tris-sucrose, Tris-glycine, and glycine buffers, Most preferably, the hydrophilic solvent is a buffered solution with some isotonicity for the self-assembled structure (to assist with retention of its phase and to be biocompatible) for in vivo use. The solvent may also comprise other components, including, for example, salts, pH buffering agents and/or sugars such as glucose and sucrose.

As mentioned above, the self-assembled structures may be used in the form of a particle, or suspension of particles. In some circumstances with certain amphiphiles, bulk phases, such as bicontinuous cubic are difficult materials to handle and are too viscous for direct administration. However, the cubic and hexagonal phases can be fragmented or dispersed into stable particles that retain the parent liquid crystalline bulk structure. In some embodiments the particle is a submicron sized nanoparticle. In alternate terms, the self-assembled structure may take the form of a colloidal dispersion (the self-assembled structure) in a continuous phase (the hydrophilic solvent). Thus, the particles in solution may be referred to as a particle suspension, a particle solution, a colloid suspension, a colloid solution, a colloid system, a particle dispersion, a nanoparticle dispersion, a nanostructured particle dispersion, a lyotropic liquid crystalline dispersion, an emulsion (liquid in liquid) or sol (solid in liquid).

Particles can be made from the bulk materials using any number of techniques known to those skilled in the art (see, for example, Spicer 2001, and U.S. Pat. No. 5,531,925). Typically, particles can be made by sonication, extrusion or high pressure homogenization. Particles typically require stabilising compounds which coat each particle to assist with the prevention of agglomeration or co-aggregation. Typical stabilising agents include block copolymers such as polyethylene oxide based polymers (ie Poloxamer) and their inclusion to stabilise particles may be necessary. Typically they are included in the mixing of the amphiphilic compound with the solvent before any dispersion takes place. The particles that may be generated by this invention have a diameter (or z-average) ranging from about 10 nm to about 500 nm, preferably about 200 nm.

As used herein, except where the context requires otherwise, the term "comprise" and variations of the term, such as "comprising", "comprises" and "comprised", are not intended to exclude further additives, components, integers or steps.

It will be understood that the invention disclosed and defined in this specification extends to all alternative combinations of two or more of the individual features mentioned or evident from the text or figures. All of these different combinations constitute various alternative aspects of the invention.

Further aspects of the present invention and further embodiments of the aspects described in the preceding paragraphs will become apparent from the following description, given by way of example and with reference to the accompanying drawings.

DETAILED DESCRIPTION OF THE INVENTIONS

Figure 1:
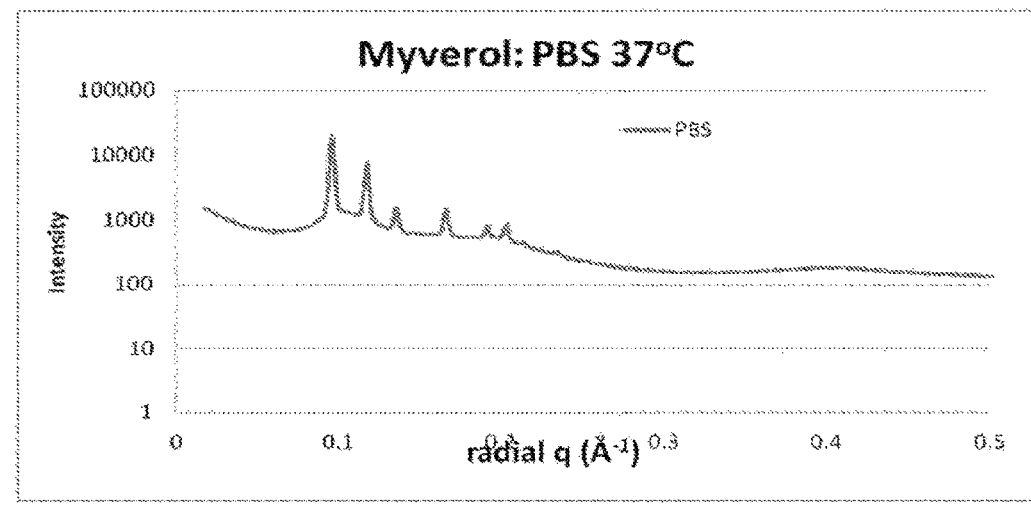
FIG. 1 shows integrated diffraction pattern of Myverol™ at 37° C. with 66 wt % phosphate buffered saline (PBS)—excess water. Integrated data with Bragg peaks and peak assignment showing diamond inverse bicontinuous cubic phase (Pn3m spacegroup) with a lattice parameter of 92.9 Å.

The inventors have discovered that one method of overcoming the dosage limitation of niacin compounds caused by their adverse side effects is to administer niacin compounds in the form of a self-assembled bulk material or a self-assembled particle (these are herein referred to collectively as self-assembled structures unless otherwise specified). The formation of a self-assembled structure comprising a niacin compound has the advantage that the pharmacological activity of the niacin compound is achieved at lower dosages as compared to dosage methods presently known in the art.

The self-assembled structures of the present invention are a self-assembled bulk material or self-assembled particles of a certain phase including a niacin compound. Typically, a bulk material having a certain phase will form from an amphiphile, that is, a molecule that possesses both a hydrophilic portion and a hydrophobic portion. The self-assembly behaviour of amphiphiles in solvent arises because of the preferential interaction between the solvent and either the hydrophilic or hydrophobic portion of the amphiphilic molecule. When an amphiphile is exposed to a polar solvent, the hydrophilic portion of the amphiphile tends to preferentially interact with the polar solvent, resulting in the formation of hydrophilic domains. The hydrophobic portion of the amphiphile molecules tend to be excluded from this domain, resulting in the de facto formation of a hydrophobic domain. Accordingly, self-assembled structures can generally not be formed by simply mixing an amphiphile with an active, such as niacin, in a solvent such as water. Various parameters must be met in order to generate the conditions for self-assembly. These can be predicted to some extent but will generally require empirical validation. The present inventors formed compositions of dispersed lyotropic liquid crystalline particles in an ethanolic solution of Myverol™ and niacin. An alternative to Myverol™ is Rylo MG19™ which is also a mono- and di-oleic acid glycerol ester. In some compositions, oleic acid was substituted for half of the Myverol™ and in some compositions calcium was added as well. The compositions were then added to excess PBS. These demonstrated burst release of niacin. As a result, these showed that niacin release was not controlled by simply adding materials that may have been expected to slow its release, such as calcium (as a chelator) or free fatty acid (eg oleic acid).

It is in a self-assembled form that, amphiphiles are capable of acting as an inert carrier or matrix into which biologically active molecules, such as a niacin compound, may be incorporated. The nanoscale porosity of the self-assembled materials provides a high internal and external surface area. A niacin compound that is distributed within a region of this material is distributed in an ordered arrangement, and at a high loading concentration due to the large internal and external liquid crystal surface area. Self-assembled structures may exhibit a variety of orientational orders. If long-range orientational order is observed within the self-assembled structure at equilibrium, the self-assembled structure is termed a 'mesophase', a 'lyotropic liquid crystalline phase', a 'lyotropic phase' or, as used herein, simply a 'phase'.

There are 2 principal types of liquid crystalline phases: thermotropic liquid crystals and lyotropic liquid crystals. Thermotropic liquid crystals can be formed by heating a crystalline solid or by cooling an isotropic melt of an appropriate solute. Lyotropic liquid crystals may be formed by addition of a solvent to an appropriate solid or liquid amphiphile. The manipulation of parameters such as amphiphile concentration and chemical structure, solvent composition, temperature and pressure may result in the amphiphile-solvent mixture adopting lyotropic phases with distinctive characteristics.

Examples of particular phases that can be formed by self-assembled structures as set out above. The bulk phases described above may be dispersed to form colloidal particles (so-called 'colloidosomes') that retain the internal structure of the non-dispersed bulk phase. When these particles possess the internal structure of a reversed bicontinuous cubic phase, the particles are colloquially referred to as cubosomes. Similarly, when the particles possess the internal structure of a reversed hexagonal phase, they are referred to as hexosomes. When the particles possess the internal structure of a lamellar phase, they are referred to as liposomes.

Whilst the bulk materials can be of use in some circumstances, the use of bulk materials having cubic phases in drug administration is limited by their high viscosity making them difficult to administer. In these cases, colloidal dispersions of particles of these cubic phases may be used in drug delivery. More preferred phases for use as drug delivery vehicles are bicontinuous cubic phase or reversed hexagonal phase. The inverse cubic phase affords distinct aqueous regions that form two continuous water networks (or channels) throughout the cubic phase that more readily allow diffusion of the niacin compound. The inverse cubic liquid crystal phase is thermodynamically stable and co-exists in equilibrium with excess water over a broad temperature range. Alternatively if the bicontinuous cubic phase is viscous and difficult to administer it may be possible to administer a lamellar phase material that converts into the cubic phase upon dissolution with aqueous, water rich, body fluids (thus facilitating the conversion of one phase to another). For example, a suitable material is a phospholipid such as 1,2-dioleoyl-sty-glycero-3-phosphocholine. The cubic phase in situ provides a viscous depot from which the niacin compound can slowly be released. An inverse cubic liquid crystal phase provides an appropriate scaffold in which to distribute or load the niacin compound owing to the high surface area of the internal liquid crystal structure (up to 400 m$^2$/g).

The self-assembled structures of the current invention may also comprise at least one other component intended to stabilise the self-assembled structure. Examples of stabilising reagents are triblock copolymers of PEG-PPO-PEG of different building blocks and more specifically poloxamer 407, as well as PEG lipid stabilising reagents such as polysorbate (for example, polysorbate 80).

When the niacin compound is formulated as part of a self-assembled structure, it is possible to administer doses of the niacin compound, in the range of about 100 mg to about 1,000 mg, preferably 250 mg to 500 mg, and achieve plasma concentrations in the range of about 0.1 to about 20 µg/mL following administration. The inventors also believe a further advantage is the sustained release of the niacin compound from the self-assembled structure over time, preferably about 1 to about 12 hours, more preferably 6 to 8 hours (ie, the bioavailability of the niacin compound is spread over a larger amount of time at lower plasma concentrations thereby minimising adverse side effects).

The invention is also directed towards administration of a self-assembled structure including a niacin compound in a buccal dosage form. Buccal administration avoids first pass metabolism. By administering a self-assembled structure including a niacin compound in a buccal dosage form, lower dosages of the niacin compound may be administered as first pass metabolism is avoided, and plasma levels of the niacin compound may be lower by virtue of the slow release rate kinetics of the niacin compound from the self-assembled structure. Buccal administration of a self-assembled structure including a niacin compound provides a means for administering a niacin compound at lower therapeutic concentrations and controlling plasma concentrations of the niacin compound, thereby reducing adverse side effects. Advantageously, buccal administration of a self-assembled structure including a niacin compound at night, when cholesterol synthesis is at its peak, reduces a subject's consciousness of the adverse side effects associated with the niacin compound and simultaneously optimises efficacy of treating hyperlipidaemia.

The invention is also directed towards self-assembled structures including a niacin compound that further include supplements to reduce adverse side effects associated with niacin and/or treat hyperlipidaemia Examples, of particular co-products include but are not limited to: flavonoids, statins, antioxidants, vitamin E, and non-steroidal anti-inflammatory drugs. In a preferred embodiment, the co-product is an anti-inflammatory agent, more preferably a sugar cane derived extract comprising polyphenols and/or flavonoids.

The sugar cane derived extract may be produced by the process described in PCT application WO2014032100 entitled "Extraction method" filed on 28 Aug. 2013 in the name of Phytolin Pty Ltd. Briefly, the extract may be produced by a process comprising:

i) mixing a sugar cane derived product with ethanol to produce an extraction mixture comprising at least about 50% v/v ethanol, ii) allowing a precipitate to form in the extraction mixture;

iii) removing the precipitate from the extraction mixture to obtain a supernatant; and iv) removing ethanol from the supernatant to produce the extract derived from sugar cane.

The process of producing the extract may further include:

i) mixing the sugar cane derived product with ethanol to produce a preliminary extraction mixture (e.g., comprising at least about 25% v/v ethanol);

ii) allowing a precipitate to form in the preliminary extraction mixture; and iii) removing the precipitate from the preliminary extraction mixture to obtain a preliminary supernatant.

The preliminary supernatant may then be subjected to the process of the invention described above.

In a preferred embodiment, the extract may be combined with the pharmaceutical composition according to the invention to counteract the inflammatory effects of niacin. By way of example, the extract, preferably in the form of a liquid extract, can be sprayed onto the pharmaceutical dosage form. As will be apparent to a skilled person, a powder, such as a freeze dried powder or dehydrated powder, can be used in place of a liquid extract.

The term 'self-assembled structure' as used throughout the specification is understood to mean an aggregate of amphiphiles that possess some degree of internal organisational order. The self-assembled structures may be formed by contacting the amphiphile with solvent. The self-assembled structure may refer to either a bulk lyotropic phase or a colloidal particle derived therefrom (a so-called 'colloidosome'). The term 'bulk phase' as used throughout the specification is understood to mean a lyotropic phase that includes but is not limited to: micellar cubic ($I_1$); normal hexagonal ($H_1$); bicontinuous cubic ($V_1$); lamellar ($L_\alpha$); reversed bicontinuous cubic ($v_2$); reversed hexagonal ($H_2$); reversed micellar cubic ($I_2$) and sponge ($L_3$) phases.

The term 'colloidal particle' as used throughout the specification is to be understood to refer to 'colloidosomes' and solid lipid particles. The term 'colloidosome' as used throughout the specification is to be understood to refer to a colloidal particle that possesses the same internal nanostructure of a bulk lyotropic phase. It will be understood that the term 'particle' refers to particles that may be nanoparticles or microparticles based on their average size, typically less than about 1 am, preferably in a range of about 10 nm to about 500 nm, more commonly about 200 nm. Solid lipid nanoparticles are a dispersed crystalline lamellar lipidic material.

The term 'cubic phase' as used throughout the specification is understood to refer to two main classes of phases: micellar cubic and bicontinuous cubic. 'Micellar cubic phase' refers to a phase consisting of spherical micelles arranged in a cubic array. A 'normal micellar cubic phase' or '$I_I$ phase' consists of spherical normal micelles arranged in a cubic array, whilst an 'inverse micellar cubic phase' or '$I_{II}$ phase' consists of spherical inverse micelles arranged in a cubic array. 'Bicontinuous cubic phase' refers to a family of closely related phases that consist of a single curved lipid bilayer that forms a complex network that separates the polar solvent space into two continuous, but non-intersecting volumes. Bicontinuous cubic phases possess long range order based upon a cubic unit cell. Bicontinuous cubic phases have zero mean curvature; that is, at all points on surface of the amphiphile bilayer, the surface is as convex as it is concave. Bicontinuous cubic phases may be of the normal ('$v_I$ phase') or reverse ('$v_{II}$ phase') type. Several types of long range orientational orders have been observed for bicontinuous cubic phases; the orientational order in these phases correspond to space groups Ia3d, Pn3m, and Im3m. When a colloidosome possesses the internal structure of a bulk cubic phase the colloidosome may be referred to as a 'cubosome'.

The term 'hexagonal phase' as used throughout the specification is to be understood to mean an amphiphile phase consisting of long, rod-like micelles packed into a hexagonal array. A 'normal hexagonal phase' is a hexagonal phase consisting of long, rod-like normal micelles, whilst an 'inverse hexagonal phase' is a hexagonal phase consisting of long, rod-like inverse micelles. The normal hexagonal phase may be referred to as the '$H_I$ phase' and the inverse hexagonal phase may be referred to as the '$H_{II}$ phase'. When a colloidosome possesses the internal structure of a bulk hexagonal phase the colloidosome may be referred to as a 'hexosome'.

The term 'lamellar phase' as used throughout the specification is to be understood to mean a stacked bilayer arrangement, where opposing monolayers of the hydrophilic portion of amphiphile molecules are separated by a polar solvent domain, while the hydrophobic portion of the amphiphile molecule of the back-to-back layers are in intimate contact to form a hydrophobic layer. The planar lamellar phase is referred to as the '$L_\alpha$' phase', There are three lamellar phases, (1) the fluid lamellar phase ($L_\alpha$) where the chains are melted, (2) the gel lamellar phase ($L_\beta$) where the chains are mostly melted but some degree of short range order and (3) the lamellar crystalline phase ($L_c$), where the chains are crystalline with very short range order.

The term 'sponge phase' or '$L_3$ phase' as used throughout the specification refers to a phase that resembles a bicontinuous cubic phase, in that it possesses an amphiphile bilayer that separates the polar solvent space into two unconnected volumes, but it does not possess long range order. Accordingly, these phases are analogous to a 'melted cubic phase'.

The term 'prodrug' as used throughout the specification refers to a biologically active agent including structural modifications thereto, such that in vivo the prodrug is converted, for example, by hydrolytic, oxidative, reductive or enzymatic cleavage to the biologically active agent by one or more reactions or steps. It includes an agent that requires one or more chemical conversion steps or steps of metabolism to produce the active molecule—that is, this term is also understood to encompass 'pre-prodrugs'.

The term 'pharmaceutical composition' as used throughout the specification means a composition comprising a therapeutically effective amount of at least one niacin compound according to the current invention. The pharmaceutical composition may further include one or more of a pharmaceutically acceptable carrier, excipient, diluent, additive or vehicle selected based upon the intended form of administration, and consistent with conventional pharmaceutical practices. Suitable pharmaceutical carriers, excipients, diluents, additives and vehicles are known to those skilled in the art and are described in publications, such as, for example Remington (Remington. The Science and Practice of Pharmacy, 21st Ed, University of the Sciences in Philadelphia (ads), Lippincott Williams & Wilkins, Philadelphia, Pa., 2005.).

As used herein, 'therapeutically effective amount' relates to the amount or dose of a niacin compound or composition thereof that will lead to one or more desired effects, in particular the reduction of cholesterol synthesis. A therapeutically effective amount of a niacin compound will vary according to factors such as the disease state, age, sex, and weight of a subject, and the ability of the substance to elicit a desired response in the subject.

The term 'buccal' as used throughout the specification refers to the absorption of an active compound across one or more membranes in the buccal cavity, including the buccal mucosa, buccal gingival, mucous membrane of the tongue, sublingual membrane and the soft palate. The term 'buccal' is used in its broadest sense to refer to the oral cavity as a whole and includes sublingual and sublabial.

EXAMPLES

Pre-Hydrated Self-Assembled Structure

A 100.00 mg/mL solution of niacin was made up in Milli Q water (18.2 MO). The desired quantity of this solution was added to Myverol™ (and in a later example with a Myverol & oleic acid mixture) to form a pre-hydrated self-assembled structure, followed by vigorous mixing and overnight equilibration. The release of niacin over time from the self-assembled structure was established by placing the composition in excess PBS as described below. To assess the rate of niacin release, a small aliquot was removed at predetermined time intervals and replaced with an equivalent volume of PBS to retain a constant volume.

First, however, to determine the form of this structure, the internal liquid crystalline structure of the dispersed particles was determined using small angle X-ray scattering (SAXS). Samples were transferred to a stainless steel paste cell (approx 1.5 mm diameter, 1 mm sample thickness) and sealed with Kapton tape on both sides. The paste cells were then attached to a thermostatted metal heating block controlled by a waterbath to ±0.1° C. Sample temperature was established by a thermocouple inserted into a spare sample position in the holder also sealed with Kapton tape. Data was collected using the SAXS/WAXS beam line at the Australian Synchrotron using a beam wavelength λ=1.0322 Å (15.0 keV) with a typical flux of 1013 photons/s, 2D diffraction patterns were recorded on a Dectris-Pilatus 1 M detector of 10 modules. The detector was offset to access a greater q-range. A silver behenate standard (A=58.38 Å) was used to calibrate the reciprocal space vector. The samples were loaded in special glass 1.5 mm capillaries (Hampton Research, USA) and positioned in a custom designed high throughput capillary holder capable of holding 34 capillaries with temperature controlled to ±0.1° C. between 20 and 75° C. Temperature control was via a re-circulating water bath (Julabo, Germany). Exposure time for each sample was 1 s. SAXS data was analysed using an IDL-based AXcess software package, developed by Dr Heron at Imperial College, London. (Seddon, Squires et al. 2006).

Figure 2:
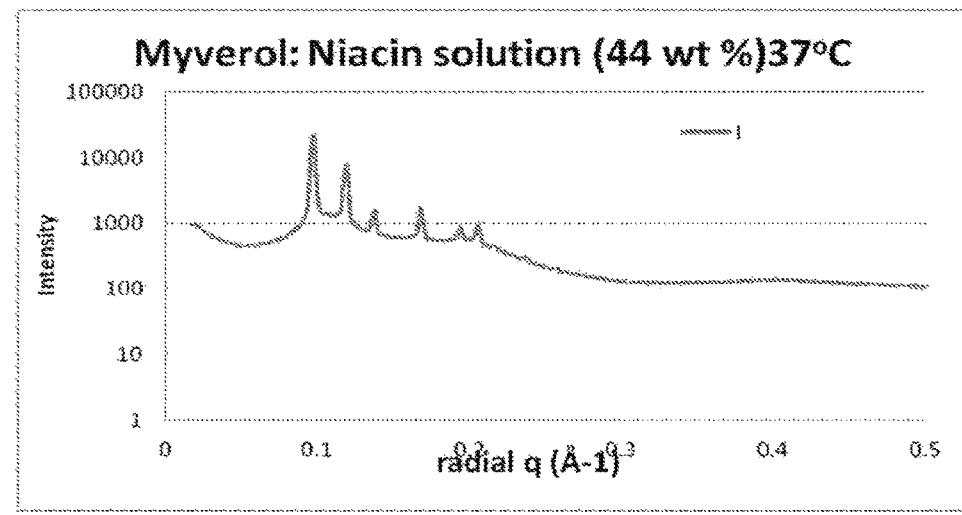
FIG. 2 shows integrated diffraction pattern of Myverol™ at 37° C. with 44 wt % 100 mg/mL niacin solution—excess water. Integrated data with Bragg peaks and peak assignment showing diamond inverse bicontinuous cubic phase (Pn3m spacegroup) with a lattice parameter of 92.9 Å.
Figure 3:
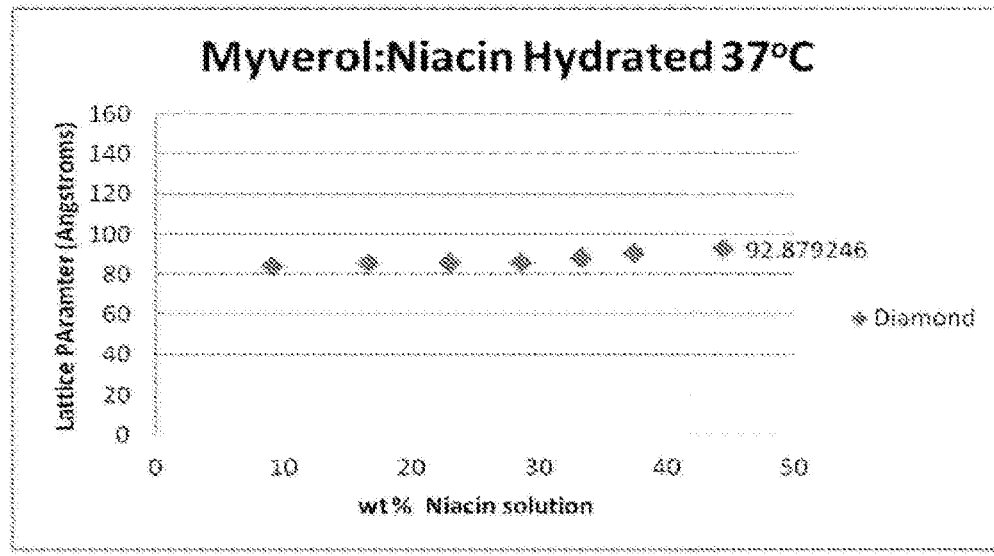
FIG. 3 shows lattice parameters of the double diamond cubic phase as a function of wt % niacin solution at 37° C.
Figure 4:
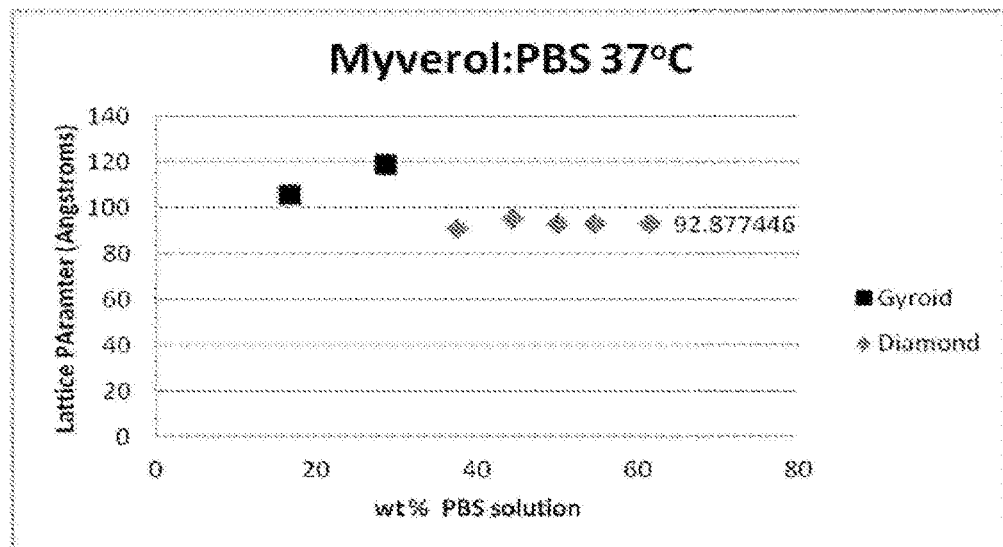
FIG. 4 shows lattice parameters of the gyroid and double diamond cubic phase as a function of wt % phosphate buffered saline (PBS) solution at 37° C.

Myverol™ in phosphate buffered saline adopts a diamond reversed bicontinuous cubic phase at 37° C. in the presence of excess hydration (FIG. 1). This phase structure is maintained when 44 wt % of 100 mg/mL of niacin is included in the aqueous phase (FIG. 2), such that there is 4.4% w/w niacin, 39.6% w/w water and 56% w/w Myverol™. Similar results were obtained at room temperature. The effect of the amount of aqueous solvent present in the pre-hydrated self-assembled structure on the phase structure affected the size of the water channels of the self-assembled materials by increasing them as the water content increases (FIG. 3). FIG. 3 also shows that the materials retained their self-assembly properties despite the extensive loading of niacin. FIG. 4 shows that, the Myverol™ in PBS at 37° C. forms a double diamond inverse bi-continuous cubic phase, although some gyroid form is produced at lower weight % PBS concentrations. The same diamond form is maintained when niacin is added as shown in FIG. 3.

To assess the release profile of niacin from the self-assembled structure, the pre-hydrated self-assembled structure was mixed and equilibrated overnight. Using a Myverol™ amphiphilic compound hydrated with 30 wt % of 100 mg/mL niacin solution, it was possible to measure the rate of release of niacin over time. 30 wt % hydration was chosen to prevent the presence of an excess water phase being present thus reducing burst release. In order to establish whether the release rate was adequate for desired release profile (approx. 6 hours) the release was monitored over a 24 hour period. The pre-hydrated self-assembled structure was loaded onto a solid support and placed in a vessel comprising Myverol™ amphiphilic compound and an agitating means. Solid supports with different surface areas were tested. The typical surface areas for the different solid supports were: 0.567 (small), 1.539 (medium) and 4.909 (large) cm$^2$. In this example the excess hydrophilic solvent was PBS, selected as a model for saliva, however any appropriate hydrophilic solvent may be used. It is also envisaged that the pre-hydrated self-assembled structure may be dispersed in the excess hydrophilic solvent in the absence of a solid support, although this would require that agitation ceased and particles settled, before withdrawing solvent for niacin analysis. In this embodiment, excess PBS was used without causing burst release.

Figure 5:
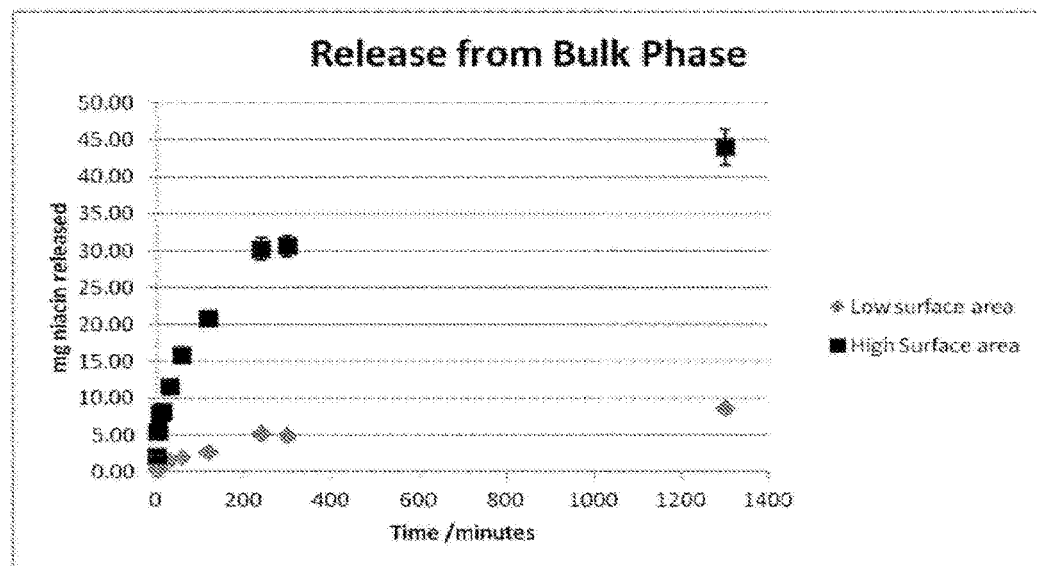
FIG. 5 shows niacin release profile from Myverol™ bulk phase system hydrated with a 30 wt % of 100 mg/mL niacin solution at 25° C. (low surface area: 0.567 $cm^2$, large surface area: 4.909 $cm^2$). N=3. Error bars indicate standard deviation.

FIG. 5 shows the release profile of two formulations. The release of niacin from the pre-hydrated self-assembled structure into the excess solvent over a 24 hour period was measured, A 200 µL aliquot of the PBS solvent, also referred to as 'release medium', was removed from the vessel at predetermined time intervals and replaced with an equivalent volume of PBS to retain a constant volume. Due to its self-assembled nature, the pre-hydrated self-assembled structures maintained their integrity during the experiment, eliminating the need to filter the samples to remove particulate matter. 100 µL of the release medium aliquot was then placed in a UV-Star 96 well-plate (half volume) and the concentration of niacin present was established by measuring the absorbance at 260 nm using the relevant calibration.

Controlled release of niacin from a pre-hydrated self-assembled structure comprising Myverol™ was observed over a 24 hour period, with a slower release profile observed for the pre-hydrated self-assembled structure loaded onto a solid support structure with a low surface area (0.567 cm$^2$) and also for a high surface area (4.909 cm$^2$). As can be seen from FIG. 5, around 30 mg of niacin had been released at the 240 and 300 minute time intervals (corresponding to the 4 to 6 hours preferred clinically). This increased to nearly 45 mg over 24 hours. The amount of surface area was also significant in that the low surface area delivery achieved release of only about 5 mg of niacin over 4 to 6 hours.

Figure 6:
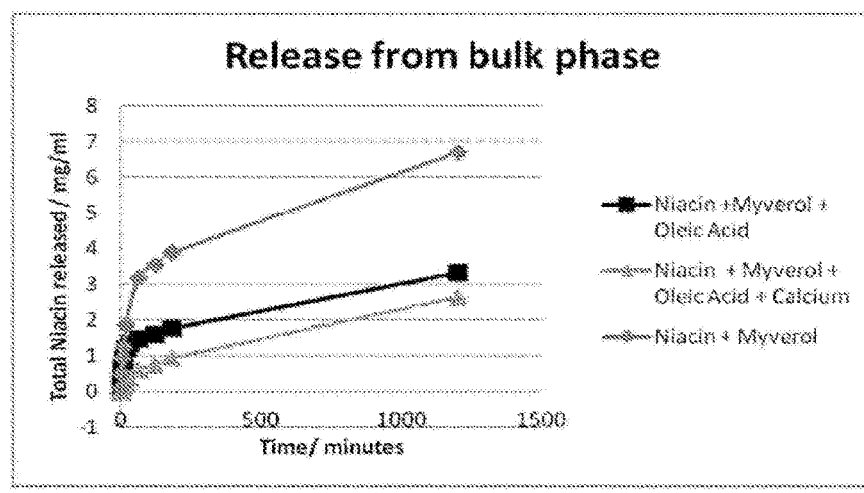
FIG. 6 shows niacin release profile from Myverol™ bulk phase system with other additives such as oleic acid (Oleic acid:Myverol™ ratio 1:4) and Calcium (II) (equimolar to niacin concentration) hydrated with a 35 wt % of 100 mg/mL niacin solution at 25° C. (low surface area: 0.567 $cm^2$, large surface area: 4.909 $cm^2$).

In order to attempt to obtain a better release profile, further compositions were tested in which different additives were included. It was necessary to minimise the amount of additive so that the concentration of niacin per gram of formulation did not decrease too low given the substantial amounts of niacin clinically required. In different formulations, oleic acid was added and also calcium was added. It can be seen from FIG. 6 that the addition of oleic acid significantly reduced the rate of release of niacin as well as the total amount released by around 50%. This occurred across all of the relevant time points (4 to 24 hours). The further addition of calcium had only a small additional effect in delaying release as also shown in FIG. 6. In FIG. 6, the composition was a 35 weight % solution of 100 mg/mL niacin at 25° C., and oleic acid was added at a ratio of 1:4 (oleic acid:Myverol™) and calcium was added in an amount equimolar to niacin.

Dry Niacin/Amphiphile Composition

Removal of water from the system allows the niacin loading concentration to be increased (and therefore reduces administration amounts), Prior to contact with an aqueous phase (either the release medium or saliva) the dry composition has no self-assembled behaviour. Once placed in contact with an aqueous phase, self-assembly of the material will occur. This process of controlled material hydration results in the controlled release of the incorporated niacin compound.

Niacin and Myverol™ 18-99K (Bronson 8 Jacobs Myverol™ 18-99K Distilled Monoglyceride) formulations were prepared as follows. The relevant masses of niacin (Sigma-Aldrich, Sydney) were mixed with melted Myverol™ (approximately 60° C.) with vigorous agitation to make a paste. The system was re-heated to 60° C. and remixed at least three times to ensure the formation of a homogenous paste. With increasing niacin concentration or ratio, the consistency of the formulation changed from a viscous paste at room temperature to a crumbling wax. The following ratios of niacin to Myverol™ were prepared:

TABLE 1

Niacin/Myverol ™ formulations prepared

| | 2 | 3 | 4 | 5 | 6 | 7 |
|---|---|---|---|---|---|---|
| wt % | 0 | 33.34 | 25 | 20 | 15 | 10 | 5 |

TABLE 1-continued

Niacin/Myverol ™ formulations prepared

| | 2 | 3 | 4 | 5 | 6 | 7 |
|---|---|---|---|---|---|---|
| Myverol ™ wt % Niacin | 0 | 66.66 | 75 | 80 | 85 | 90 | 95 |

To analyse the characteristics of the formulation interface with the aqueous domain, cross-polarised light microscopy was used. A water penetration scan using cross polarised microscopy was used to monitor the phases formed by a bulk amphiphile as water penetrates into the sample. A small amount of sample was placed between a glass slide and coverslip. Following the addition of PBS, the aqueous domain infiltrates the amphiphile, forming a concentration gradient from 100% buffer on the outer edges, to 100% lipid near the centre of the lipid drop. As the sample is hydrated, niacin dissolves and is released from the lyotropic liquid crystalline matrix. The characteristic optical textures of the various phases allows for the identification of the nanostructures of the formulation.

Figure 7:
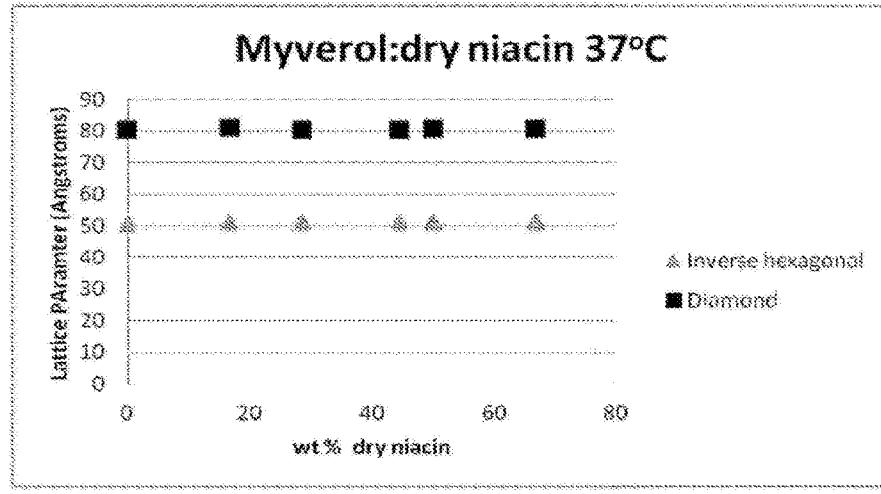
FIG. 7 shows lattice parameters of the inverse hexagonal and diamond cubic phase as a function of wt % of dry niacin with PBS solution at 37° C.
Figure 8:
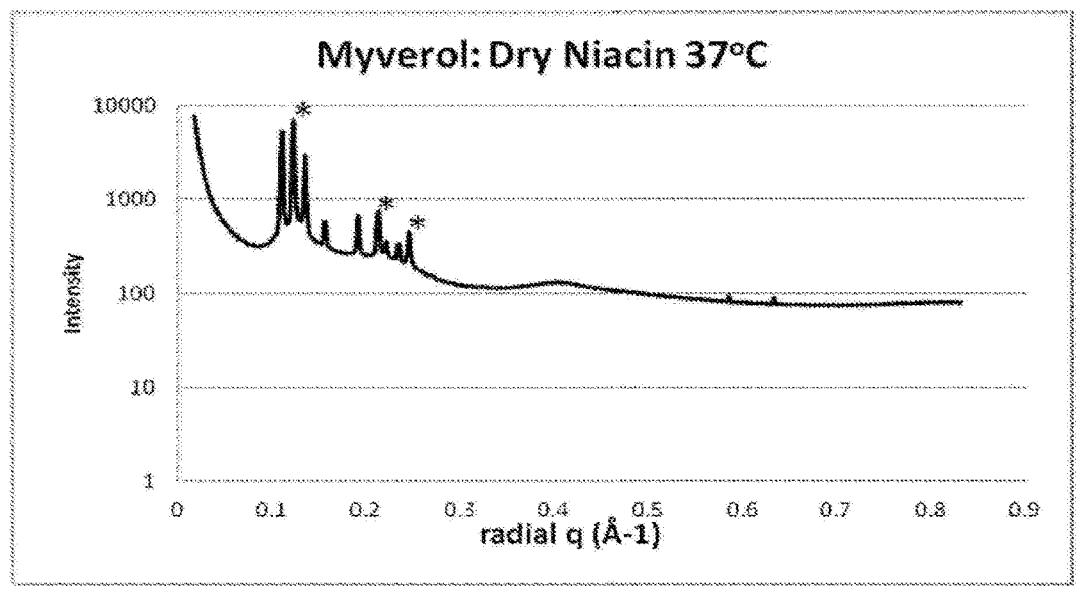
FIG. 8 shows integrated diffraction pattern of Myverol™ at 37° C. with 66 wt % niacin in the presence of slight excess PBS 37° C. Integrated data with Bragg peaks and peak assignment showing diamond inverse bicontinuous cubic phase (Pn3m spacegroup) with a lattice parameter of 80.7 Å. The inverse hexagonal phase peaks (lattice parameter 51.3) Å, 1, √3, √4, are highlighted by asterisks (*).

To establish the influence of high niacin concentrations on Myverol™ phase behaviour, formulations were prepared and hydrated with PBS to determine the phase behaviour during the hydration process. As the hydration/salvation of niacin is a dynamic process, a range of phases were observed in the Myverol™ system. SAXS measurements were then performed to confirm the phase behaviour at 25 and 37° G. Both inverse hexagonal phases and inverse bicontinuous diamond phases were observed to co-exist with the system at 37° G, as shown in FIG. 7 for formulation 2 of Table 1 in the system with high levels of niacin (66 wt %). As can be seen in FIG. 8, which is an integrated diffraction pattern at 37° C. with the formulation 2 the presence of slight excess PBS, the Bragg peaks and peak assignment showing diamond inverse bi-continuous cubic phase with lattice parameter of 80.7 angstroms can be seen, together with the inverse hexagonal phase peaks (lattice parameter 51.3 angstroms) which have been highlighted by asterisks.

Figure 9:
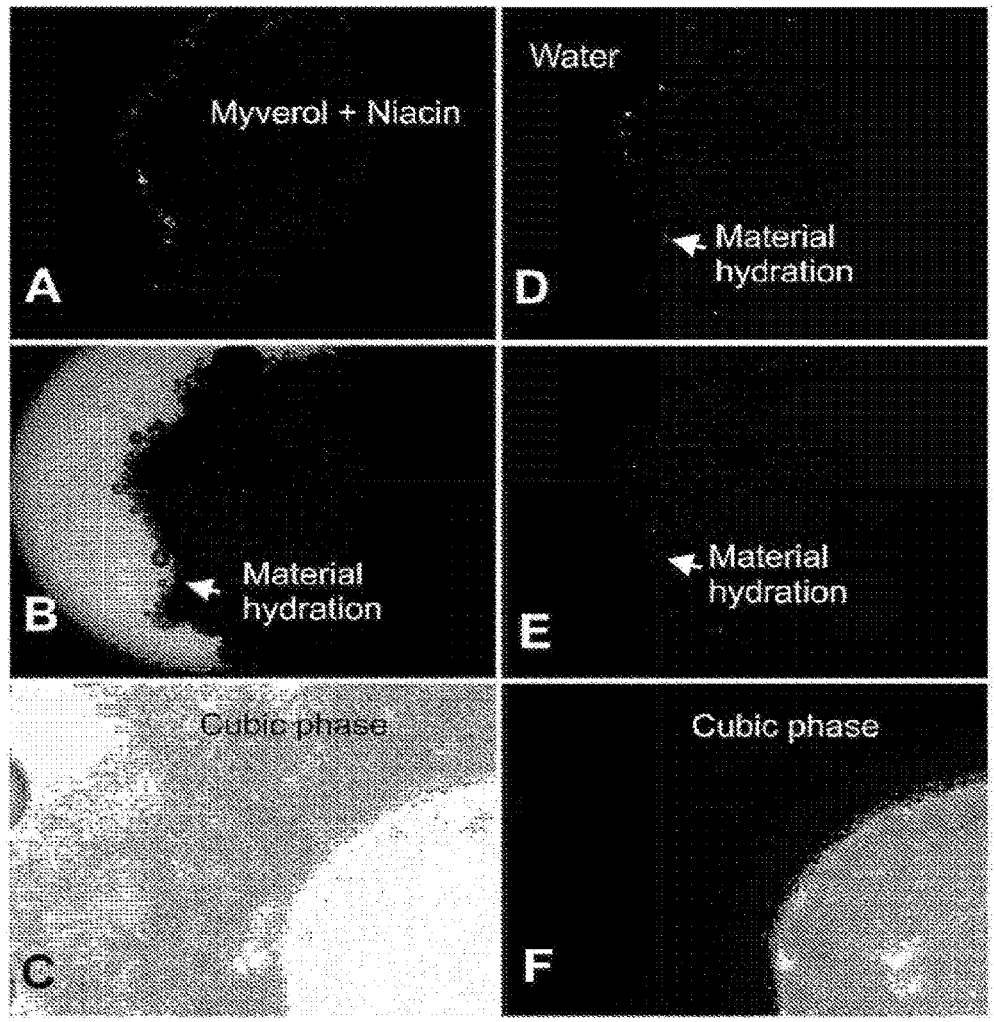
FIG. 9 shows hydration with PBS of the dry niacin: Myverol™ system observed by cross polarised light microscopy showing potential formation of the hexagonal or lamellar and cubic phase A) sample prior to hydration, B F) sample following progressive hydration of Myverol:niacin material. The brighter band at the interface of the aqueous and bulk phase material is anisotropic and can be assigned to either a lamellar or inverse hexagonal phase. Panels C & F clearly show the presence of a viscous, isotropic material identified as cubic phase.

Understanding what is happening at the interface of the Myverol™/dry niacin system is believed to be key to the properties of this formulation. A flooding experiment was conducted using cross polarised light microscopy on a sample with 80 wt % niacin in Myverol™ (FIG. 9). PBS was applied to a thin sample of material and the progress of the hydration was monitored. A bright band of birefringence was observed at the water and cubic phase interface. This band was observed to progress through the sample as material hydration continued (Panels A, B, and E in FIG. 9) and description of FIG. 9 above. In combination with SAXS data presented above, this band appears to be due to the formation of hexagonal phase.

Figure 10:
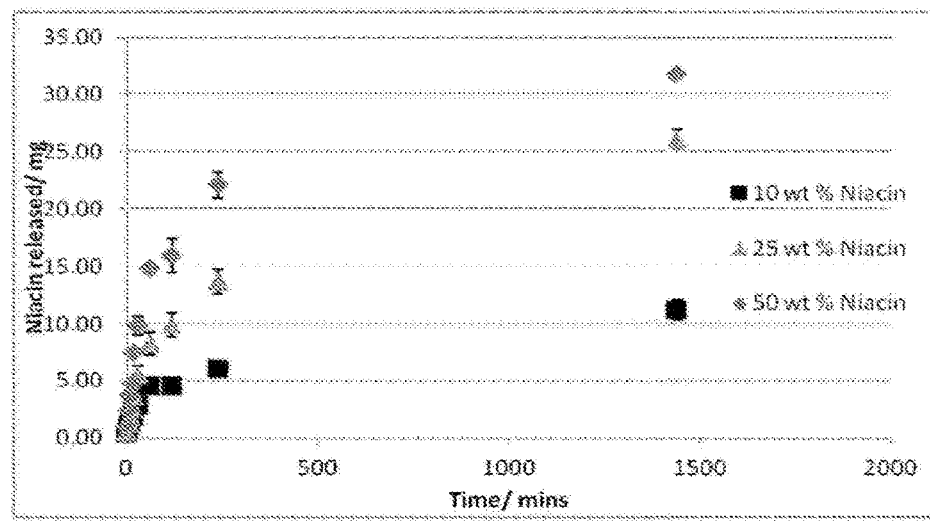
FIG. 10 shows niacin release profile from Myverol™ bulk phase system with dry niacin in release media at 25° C., 10 wt %, 25 wt % and 50 wt % niacin (small surface area: 0.567 cm$^2$). N=3, Error bars indicate standard deviation.
Figure 11:
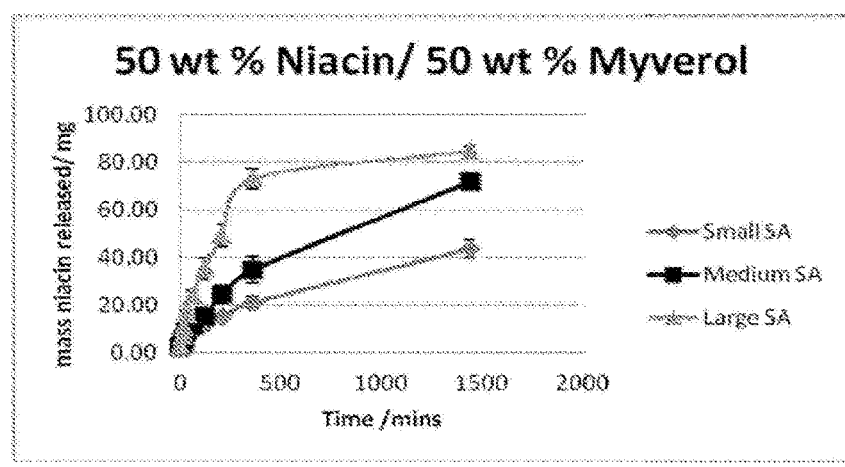
FIG. 11 shows niacin release profile from Myverol™ bulk phase system with dry niacin in release media at 25° C. (50 wt % niacin/50 wt % Myverol) (surface areas: 0.567 (small), 1.539 (medium) and 4.909 (large) cm$^2$). N=3, Error bars indicate standard deviation.
Figure 12:
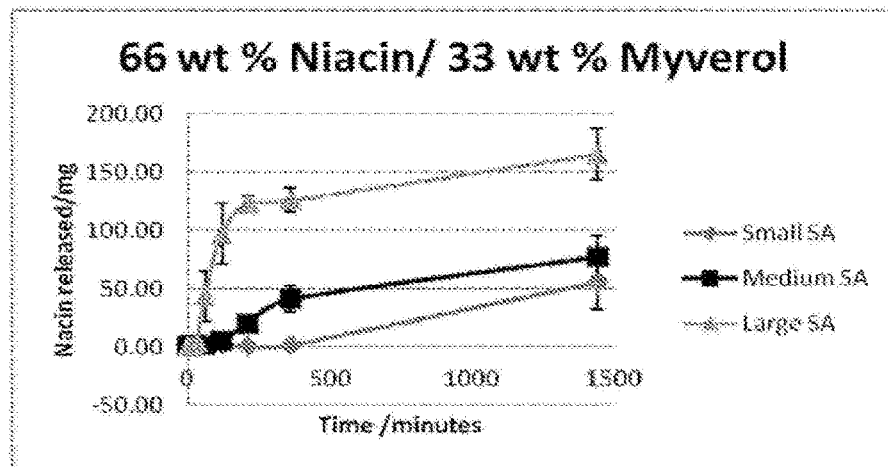
FIG. 12 shows niacin release profile from Myverol™ bulk phase system with dry niacin in release media at 25° C. (66.6 wt % niacin/33.3 wt % Myverol) (surface areas: 0.567 (small), 1.539 (medium) and 4.909 (large) cm$^2$). N=3. Error bars indicate standard deviation.
Figure 13:
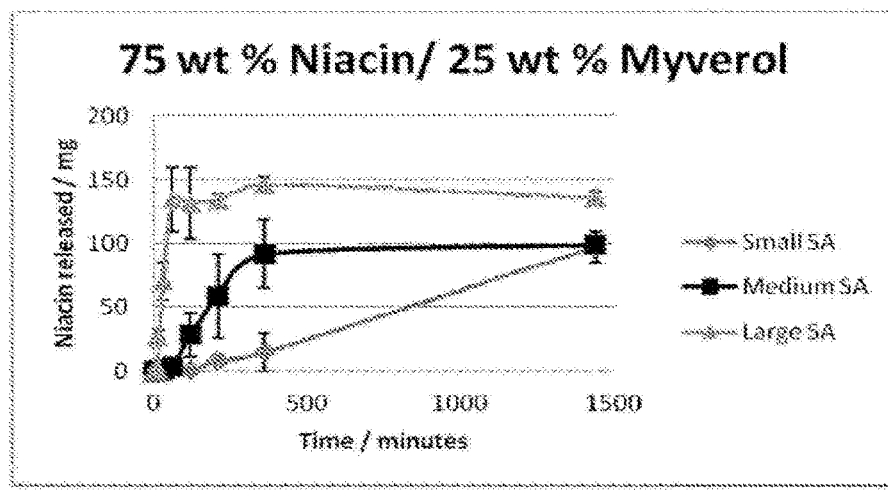
FIG. 13 shows niacin release profile from Myverol™ bulk phase system with dry niacin in release media at 25° C. (75 wt % niacin/25 wt Myverol) (surface areas: 0.567 (small), 1.539 (medium) and 4.909 (large) cm$^2$). N=3, Error bars indicate standard deviation.
Figure 14:
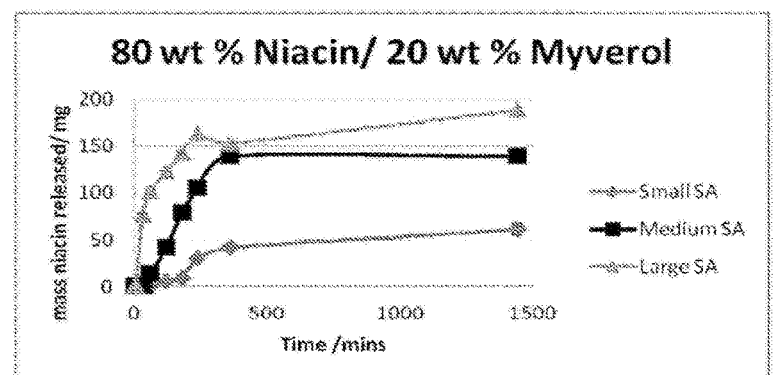
FIG. 14 shows niacin release profile from Myverol™ bulk phase system with dry niacin in release media at 25° C. (80 wt % niacin/20 wt % Myverol) (surface areas: 0.567 (small), 1.539 (medium) and 4.909 (large) cm$^2$). N=3 Error bars indicate standard deviation.
Figure 15:
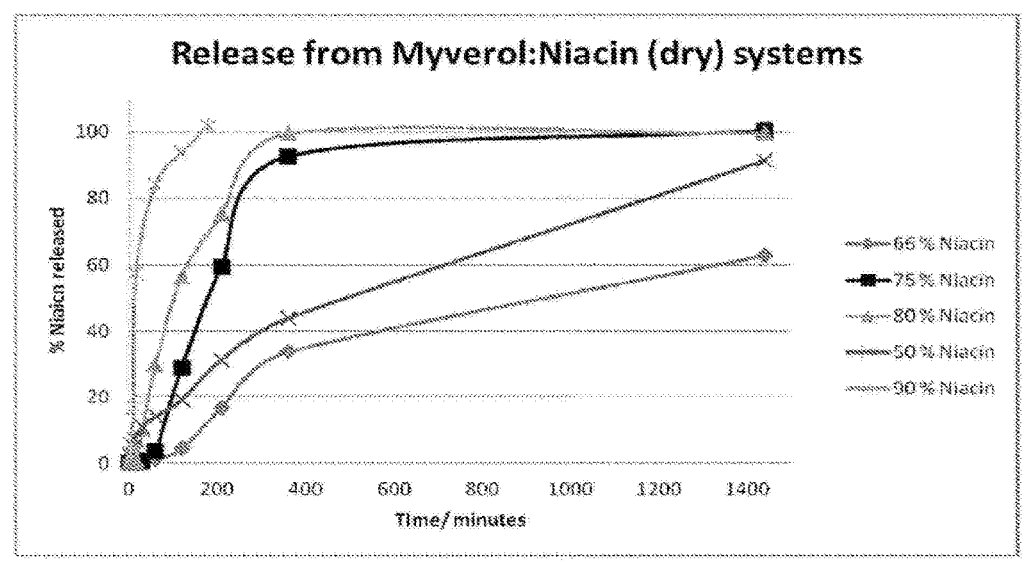
FIG. 15 shows niacin release profile from Myverol™ bulk phase system with dry niacin in release media at 25° C. (surface areas: 1.539 (medium) cm$^2$).
Figure 16:
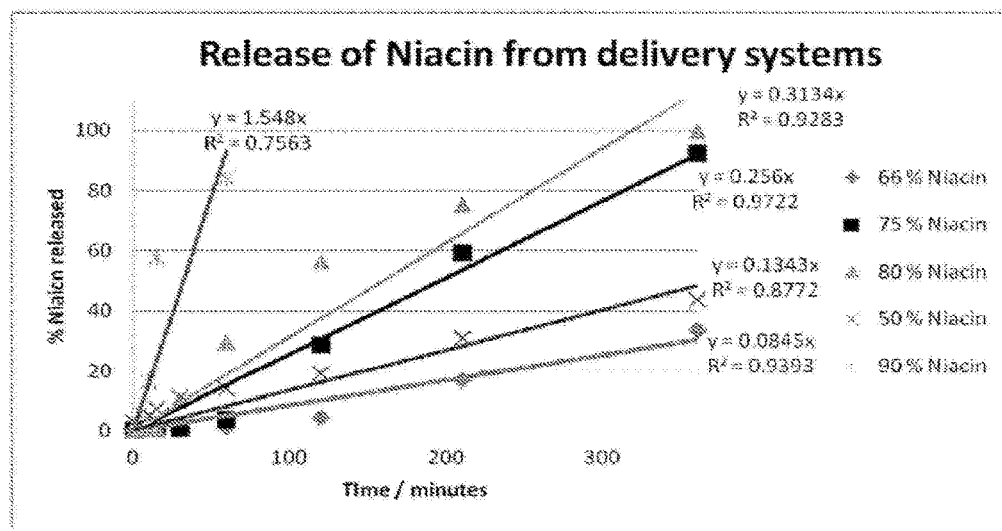
FIG. 16 shows niacin release profile from Myverol™ bulk phase system with dry niacin in release media at 25° C. (surface areas: 1.539 (medium) cm$^2$).

Once the niacin has been removed from the system, the viscous, isotropic material is indicative of the cubic phase being present. (FIG. 9 Panels D and E). The hexagonal phase, which typically has very slow release kinetics, will contribute to the controlled release of niacin. The achievable loadings were tested to ensure that the high dose desired (approx. 500 mg) was achievable Preliminary experiments at room temperature focussed on increasing the dose to assess the potential of individual formulations. Niacin levels were systematically increased up to 90 wt %; concomitant increases in surface area ensure that high niacin release levels could be established. FIG. 10 illustrates the niacin release profile from formulation 1 (50 wt % niacin) at 25° C. from a small surface area (0.567 cm$^2$). The effect of surface area was also investigated and the results are shown in FIGS. 11 to 14 for formulations 1-4 respectively across a small surface area (0.567 cm$^2$), medium surface area (1.539 cm$^2$) and large surface area (4.909 cm$^2$) to demonstrate that increasing the level of niacin permits not only an increase in the dose that is released but also an increase in the overall release levels and that surface area is a relevant parameter. FIG. 15 illustrates the release profile for formulations 1, 2, 3, 4 and 6 at 25° C. from a medium surface area (1.539 cm$^2$). It is interesting to note that the release rate of the 50 wt % niacin sample is greater than that of the 66 wt % sample. This may be due to slight changes in the phase behaviour of the system. From this data, the optimal release profile for a 4-6 hour period is a mass ratio of approximately 80:20 Niacin:Myverol™, and this enabled the release of high levels of niacin over a period of approximately 6 hours (FIG. 16).

Figure 17:
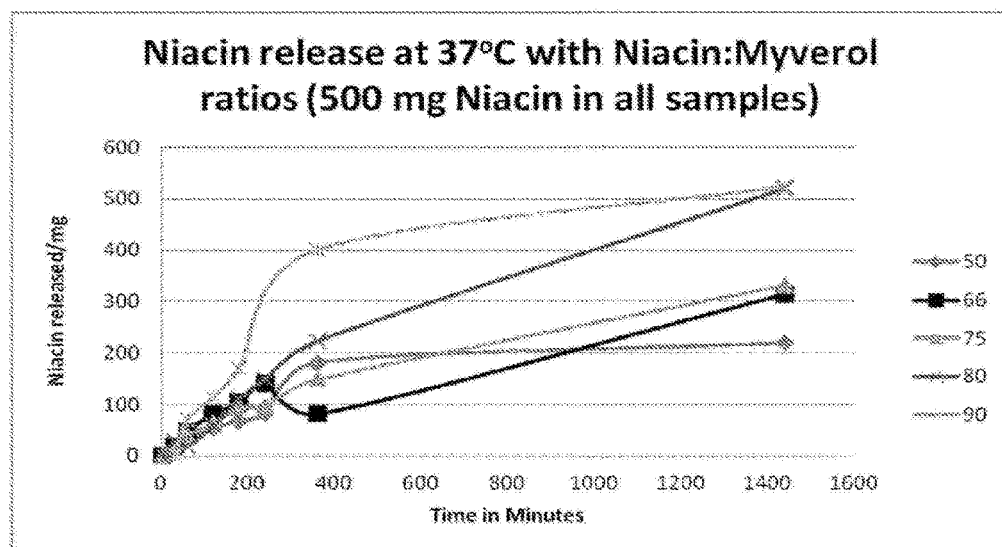
FIG. 17 shows niacin release profile from Myverol™ bulk phase system with dry niacin in release media at 37° C. (surface areas: 1.539 (medium) cm$^2$).

A clinically useful dose of niacin would be 500 mg. Formulations similar to formulations 1, 2, 3, 4 and 6 from Table 1 were made having 500 mg of niacin and the related level of Myverol™ and the release profile for niacin tested at 37° C. (in order to mimic body temperature). It can be seen from FIG. 17 that the 90 weight % formulation achieved release of 400 mg after 6 hours and the 80 weight % had release of 130 mg of niacin. These systems demonstrate that it is possible to release up to 400 mg of niacin after 6 hours in an in vitro setting into release medium.

A further additive was tested for its effect on niacin release from the niacin:Myverol™ mixture, namely ethanol. This was tested for enhanced absorption in biological systems. Thus preliminary investigations were performed to test the compatibility of loading different levels of ethanol into the Myverol:Niacin systems. In the absence of water, ethanol will not lead to self-assembly and thus no formation of nanostructure is possible. Once in the presence of water, the ethanol will readily be solubilised thus permitting the self-assembly of the amphiphilic molecules of Myverol™.

Niacin and Myverol™ 18-99K (Bronson & Jacobs Myverol™™ 18-99K Distilled Monoglyceride) formulations were prepared as follows. The relevant masses of niacin (Sigma-Aldrich, Sydney) were mixed with melted Myverol™ (approximately 60° C.) in the 80:20 mass ratio with vigorous agitation to make a paste of delivery system, typically the ratio used was as shown in the table below. The system was re-heated to 60° C. and remixed at least three times to ensure the formation of a homogenous paste. The consistency of the formulation at room temperature was from a viscous paste to a crumbling wax. Once the homogeneous delivery system mixture was formed and cooled to room temperature, ethanol was added to the mixture at the relative proportions set out in Table 2 below and, again, vigorously mixed to form an homogeneous preparation. The drug release set-up was as described previously.

TABLE 2

| Ratio mass Delivery System: mass Ethanol | |
|---|---|
| 1 | 1 |
| 2 | 1 |
| 4 | 1 |

Figure 18:
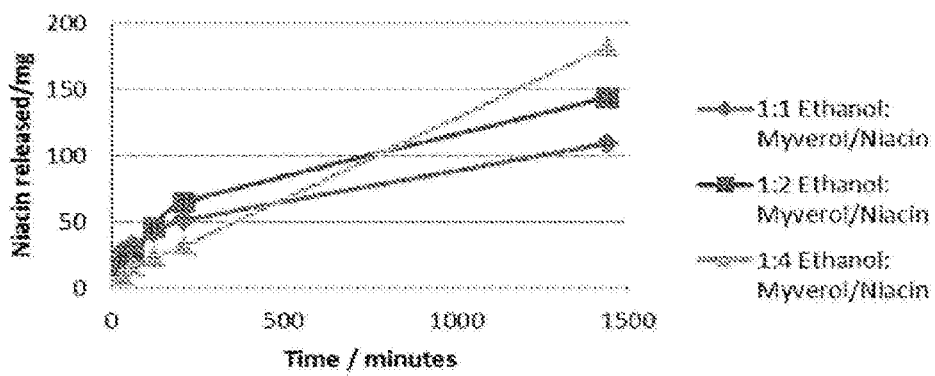
FIG. 18 shows niacin release profile from Myverol™ bulk phase system in the presence of different ethanol ratios with niacin in release media at 25° C. (surface areas: 1.539 (medium) cm$^2$).
Figure 19:
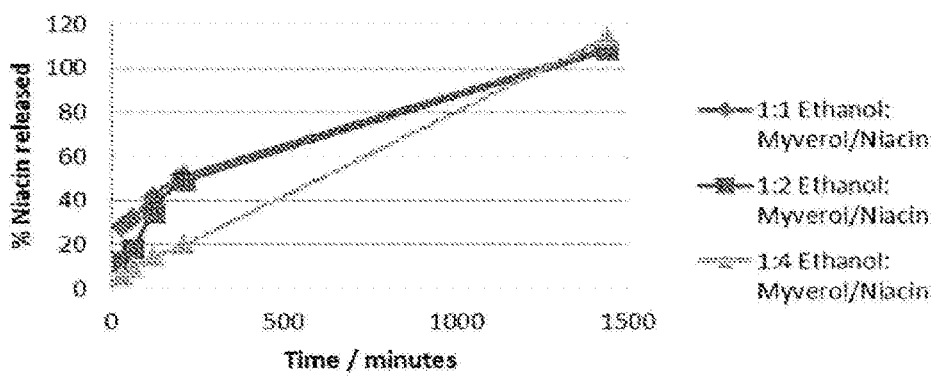
FIG. 19 shows niacin release profile, as a total percentage of niacin present, from Myverol™ bulk phase system in the presence of different ethanol ratios with niacin in release media at 25° C. (surface areas: 1.539 (medium) cm$^2$).
Figure 20:
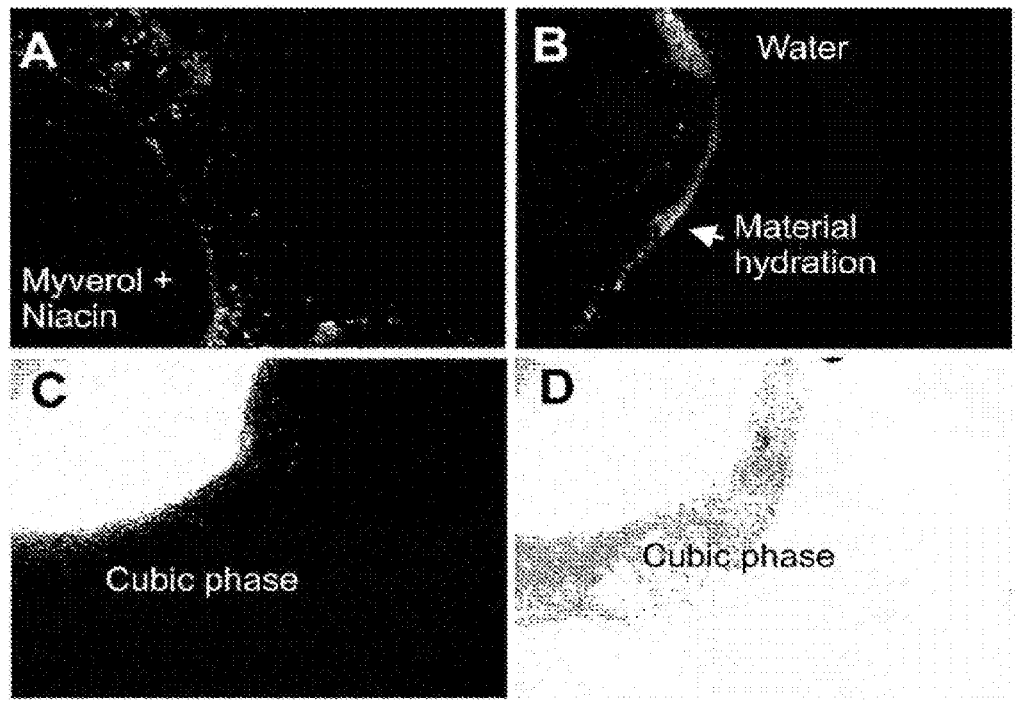
FIG. 20 shows hydration with PBS of the dry niacin (80 wt %):Myverol™ (20 wt %) system at a 4:1 ratio with ethanol observed by cross polarised light, microscopy showing potential formation of the hexagonal or lamellar and cubic phase at 37° C.

FIGS. 18 and 19 demonstrate how niacin was released controllably from this system over time at 25° C. in PBS from a medium surface area (1.539 cm$^2$) and the release rate may increase as the levels of ethanol are increased. A slight burst-release of niacin is observed in the early time period due to the presence of some solubilised niacin in the ethanol part of the system. The addition of ethanol does seem to contribute to a more rapid release of the niacin whilst still allowing for significant control of release. The addition of the lowest amount of ethanol (a 1:4 ratio with drug delivery system) was tested at 37° C. to assess drug release. The creation of an interface between the aqueous and self-assembled phase is still possible despite the presence of ethanol as shown in FIG. 20. FIG. 20 contains panels: A) sample prior to hydration, B D) sample following progressive hydration of Myverol:niacin material. The brighter band at the interface of the aqueous and bulk phase material is anisotropic and can be assigned to either a lamellar or inverse hexagonal phase. Panels C & D show the presence of a viscous, isotropic material identified as cubic phase. The final state of the material is very similar to that of the one produced in the absence of ethanol.

Figure 21:
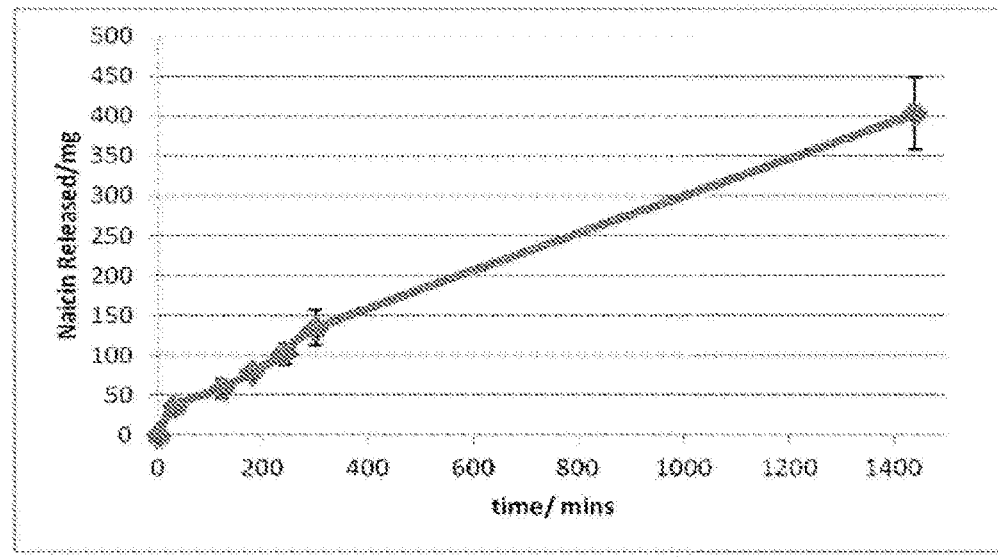
FIG. 21 shows niacin release profile from dry niacin (80 wt %):Myverol™ (20 wt %) system at a 4:1 ratio with ethanol at 37° C. (surface area: 4.909 cm$^2$) N=3, Error bars indicate standard deviation.

The release of niacin from this system (dry niacin (80 wt %): Myverol™ (20 wt %) system at a 4:1 ratio with ethanol) at 37° C. was tested as described earlier. It is clear that despite a relatively quick initial release (in the first 30 minutes), the remainder of the niacin was released in a controllable fashion (FIG. 21). This demonstrates that ethanol can be used as an additive to further control release.

PGE2 Inhibition of Sugar Cane Derived Anti-Inflammatory Extract

In a preferred embodiment of the invention, a sugar can derived extract is combined with the pharmaceutical composition of the invention to counteract the inflammatory effects of niacin. The extract may be prepared according to WO2014032100 (Phytolin Pty Ltd). The following example demonstrates the anti-inflammatory effect of the sugar cane derived extract produced in this way.

As is known in the art, prostaglandin E2 (PGE2) activity can be used to measure anti-inflammatory activity of a substance. PGE2 inhibitory activity can be measured by the ability of test samples to inhibit PGE2 production in 3T3 cells when stimulated with calcium ionophore. As understood in the art, aspirin and ibuprofen may be included in the assay as a positive control.

The in vitro production of PGE2 from 3T3 cells was measured using the Cayman Chemical Prostaglandin E2 monoclonal EIA (Enzyme Immuno Assay) kit. The cells were exposed to extracts derived from dunder and molasses and stimulated with calcium ionophore. The cell supernatants were then assayed for PGE2 production. The cell cytotoxicity of the samples was tested against 3T3 cells to confirm that the observed PGE2 inhibition was not due to cell cytotoxicity. Aspirin and ibuprofen were used as positive controls.

Figure 22:
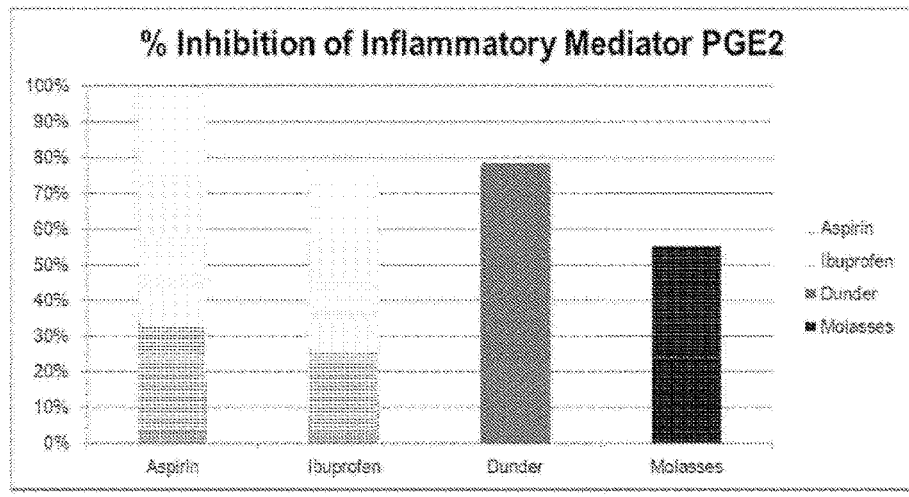
FIG. 22 shows a comparison of % PGE2 inhibition for aspirin (control), ibuprofen (control), dunder and molasses.

The highest PGE2 inhibition observed for molasses and dunder was 29.90% and 42.33%, respectively, at 0.488 µg/mL. As shown in FIG. 22, the PGE2 inhibitory response of dunder was similar to that of ibuprofen (42.14% at 0.488 µg/mL). Inhibition of PGE2 production in the cells, relative to control cells not exposed to the samples, indicates that the samples act as an anti-inflammatory agent in vitro.

Encapsulating Pravastatin in a Self-Assembled Liquid Crystalline Phase Formed by an Amphiphile Myverol™ 18-99 K (from Kerry ingredients & Flavours in Wisconsin) was used to form self-assembled structures incorporating various percentages of the active pravastatin.

To prepare the self-assembled liquid crystalline phase structures, Myverol™ was mixed with pravastatin at varying concentrations by dissolving in a 50:50 mixture of methanol and Chloroform. The mixture was placed in a roller mixer for 24 hours at 40 degrees Celsius to ensure full mixing. The mixture was then placed under vacuum at 50 degrees Celsius to remove all solvents To prepare the self-assembled liquid crystalline phase structures for SAXS measurement, 100 mg of the Myverol™ and pravastatin mixture was mixed with 200 mL of PBS at pH 7.4 for more than 36 hours to ensure full hydration. The Australian Synchrotron SAXS/WAXS beamline was used to measure the structural behaviour of the self-assembled systems at 25 and 40° C.

Pravastatin appeared to readily incorporate into the Myverol™ up to the experimental limit of 80%, that is, no visible precipitation was observed.

Figure 23:
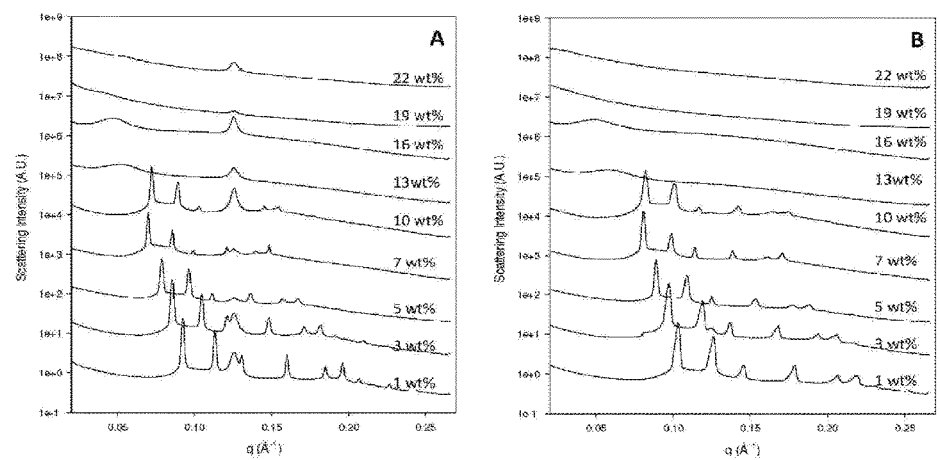
FIG. 23 shows the SAXS profile of self-assembled liquid crystalline structures with varying concentration of pravastatin, in excess water, at 25 (A) and 40 (B) degrees Celsius.

FIG. 23 shows the SAXS profile of the liquid crystalline phase structure with increasing concentration of pravastatin, in excess PBS, at 25 (Panel A) and 40 (Panel B) degrees Celsius respectively. At low pravastatin concentration, the system showed a typical SAXS profile, that is the SAXS profile indicated the presence of self-assembled structures because the profile showed the Pn3m space group, which indicates the diamond inverse bicontinuous cubic phase.

Increasing pravastatin concentration induced an expansion of the cubic crystalline lattice as evident from the Pn3m space group shifting to the left with higher concentrations of pravastatin. At higher than 10 wt % pravastatin the system lost the diamond inverse bicontinuous cubic structure.

Pravastatin was therefore shown to be capable of being included in the self-assembled liquid crystalline phase formed by the interaction of Myverol™ with hydrophilic solvents.

It will be understood that the invention disclosed and defined in this specification extends to all alternative combinations of two or more of the individual features mentioned or evident from the text or drawings. All of these different combinations constitute various alternative aspects of the invention.

REFERENCES

Clogston, J.; Rathman, J.; Tomasko, D.; Walker, H.; Caffrey. M., Phase behaviour of a monoacylgylcerol: (Myverol 18-99K)/water system. *Chemistry of Physics and Lipids* 2000, 107, 191-220.

Drummond, G. J.; Fong, C., Surfactant self-assembly objects as novel drug delivery vehicles. *Current Opinion in Colloid and Interface Science* 2000, 4(6), 449-456.

Laughlin, R. G., The Aqueous Phase Behaviour of Surfactants, Academic Press, San Diego, Calif., 1996.

Laughlin, R. G.; Lynch, M. L.; Marcott, C.; Munson; R. L.: Marrer, A. M.; Kochvar, K. A., Phase studies by Diffusive Interfacial Transport using near-infrared analysis for water (DIT-NIR). *Journal of Physical Chemistry B* 2000, 104(31), 7354-7362.

Small, D., Handbook of Lipid Research. ed, D. J. Hanahan ed.; Plenum Press, New York, 1986, Vol 4.

Spicer, P. T.; Hayden, K. L.; Lynch, M. L.; Ofori-Boateng, A.; Burns, J. L., Novel Process for Producing Cubic Liquid Crystalline Nanoparticles (Cubosomes). *Langmuir* 2001, 17(19), 5748-5756.

The claims defining the invention are as follows:

1. A method for prolonging the release of niacin in a subject, comprising:
   administering to the oral mucosa of a subject in need thereof a composition comprising an amphiphilic compound capable of self-assembling into a liquid crystalline phase upon contact with a hydrophilic solvent and a therapeutically effective amount of a niacin compound, and prolonging release of the niacin compound in the subject for up to 12 hours.

2. The method of claim 1, wherein release of the niacin compound is prolonged for 6 to 8 hours.

3. The method of claim 1, wherein release of the niacin compound is prolonged for at least 4 to 6 hours.

4. The method of claim 1, wherein the composition does not comprise prolonged release polymers.

5. The method of claim 1, wherein administering the composition comprises sublingual administration.

6. The method of claim 1, wherein the niacin compound comprises a unit dosage of 100 mg to 1,000 mg.

7. The method of claim 1, wherein the weight of the amphiphilic compound in the composition when dry comprises at least 5% by weight of the combined weight of the dry niacin compound and the dry amphiphilic compound in the composition.

8. The method of claim 1, wherein the weight of niacin compound when dry comprises at least 50% by weight of the combined weight of the dry niacin compound and the dry amphiphilic compound.

9. The method of claim 1, wherein administering the composition comprises nighttime administration.

10. The method of claim 1, wherein the niacin compound comprises nicotinyl alcohol tartrate, d-glucitol hexanicotinate, aluminium nicotinate, niceritrol, or d,l-alpha-tocopheryl nicotinate.

11. The method of claim 1, wherein the niacin compound comprises niacin.

12. The method of claim 1, wherein the amphiphilic compound comprises a monoglyceride of a fatty acid comprising a 6 to 24 carbon chain, a diglyceride of a fatty acid comprising a 6 to 24 carbon chain, or a combination thereof.

13. The method of claim 12, wherein the carbon chain is unsaturated.

14. The method of claim 12, wherein the amphiphilic compound comprises a mixture of monoacylglycerols, diacylglycerols, and glycerol.

15. The method of claim 12, wherein the amphiphilic compound comprises a glycerol monooleate.

16. The method of claim 1, wherein contacting the composition with excess PBS causes the composition to physically disintegrate and the amphiphilic compound to form a self-assembled structure detectable by small angle x-ray scattering (SAXS).

17. The method of claim 16, wherein the detectable self-assembled structure comprises an inverse hexagonal bulk phase.

18. The method of claim 16, wherein disintegration of the composition comprises 2 to 10 minutes.

19. The method of claim 1, wherein the composition is a tablet.

20. The method of claim 1, wherein the amphiphilic compound is self-assembled.

21. The method of claim 1, wherein the composition is a colloidal dispersion, wherein the colloidal dispersion comprises a self-assembled amphiphilic compound in a continuous phase formed by one or more hydrophilic solvents.

* * * * *